(12) United States Patent
Nelson et al.

(10) Patent No.: US 10,196,674 B2
(45) Date of Patent: *Feb. 5, 2019

(54) MULTIPHASE NUCLEIC ACID AMPLIFICATION

(71) Applicant: GEN-PROBE INCORPORATED, San Diego, CA (US)

(72) Inventors: Norman C. Nelson, San Diego, CA (US); Lyle J. Arnold, Jr., Poway, CA (US); Lizhong Dai, San Diego, CA (US); Steven Phelps, La Jolla, CA (US); Jijumon Chelliserry, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 415 days.

This patent is subject to a terminal disclaimer.

(21) Appl. No.: 14/856,339

(22) Filed: Sep. 16, 2015

(65) Prior Publication Data

US 2016/0002709 A1    Jan. 7, 2016

Related U.S. Application Data

(62) Division of application No. 14/014,607, filed on Aug. 30, 2013, now Pat. No. 9,139,870.

(Continued)

(51) Int. Cl.
*C12Q 1/68* (2018.01)
*C12Q 1/6806* (2018.01)
(Continued)

(52) U.S. Cl.
CPC ............ *C12Q 1/6806* (2013.01); *C12P 19/34* (2013.01); *C12Q 1/68* (2013.01); *C12Q 1/6825* (2013.01);

(Continued)

(58) Field of Classification Search
CPC ....................................................... C12Q 1/68
See application file for complete search history.

(56) References Cited

U.S. PATENT DOCUMENTS 5,210,015 A    5/1993   Gelfand et al.
5,487,972 A    1/1996   Gelfand et al.
(Continued)

FOREIGN PATENT DOCUMENTS

WO    2002-059353 A2    8/2002
WO    2007-146154 A1    12/2007
(Continued)

OTHER PUBLICATIONS

Sanchez et al. (PNAS, 2004, 101(7):1933-1938).*

(Continued)

*Primary Examiner* — Stephanie K Mummert
(74) *Attorney, Agent, or Firm* — Michael J. Gilly; Brian S. Sun

(57) ABSTRACT

Improved methods for use in nucleic acid amplification, including multiplex amplification, where the amplification is carried out in two or more distinct phases are disclosed. The first phase amplification reaction preferably lacks one or more components required for exponential amplification. The lacking component is subsequently provided in a second, third or further phase(s) of amplification, resulting in a rapid exponential amplification reaction. The multiphase protocol results in faster and more sensitive detection and lower variability at low analyte concentrations. Compositions for carrying out the claimed methods are also disclosed.

14 Claims, 30 Drawing Sheets

Related U.S. Application Data

(60) Provisional application No. 61/695,106, filed on Aug. 30, 2012, provisional application No. 61/846,538, filed on Jul. 15, 2013.

(51) Int. Cl.
  *C12Q 1/6848* (2018.01)
  *C12Q 1/70* (2006.01)
  *C12P 19/34* (2006.01)
  *C12Q 1/6865* (2018.01)
  *C12Q 1/6825* (2018.01)

(52) U.S. Cl.
  CPC ......... *C12Q 1/6848* (2013.01); *C12Q 1/6865* (2013.01); *C12Q 1/70* (2013.01)

(56) References Cited

U.S. PATENT DOCUMENTS

| | | |
|---|---|---|
| 5,656,462 A | 8/1997 | Keller et al. |
| 5,712,385 A | 1/1998 | McDonough et al. |
| 5,804,375 A | 9/1998 | Gelfand et al. |
| 5,856,088 A | 1/1999 | McDonough et al. |
| 6,252,059 B1 | 6/2001 | McDonough et al. |
| 6,582,920 B2 | 6/2003 | Yang et al. |
| 6,589,734 B1 | 7/2003 | Kacian et al. |
| 6,605,451 B1 | 8/2003 | Marmaro et al. |
| 6,623,920 B1 | 9/2003 | Bee et al. |
| 6,649,749 B2 | 11/2003 | McDonough et al. |
| 6,844,158 B1 | 1/2005 | Mitsuhashi |
| 6,946,254 B2 | 9/2005 | Yang et al. |
| 7,083,922 B2 | 8/2006 | Kacian et al. |
| 7,087,414 B2 | 8/2006 | Gerdes et al. |
| 7,097,979 B2 | 8/2006 | Bee et al. |
| 7,255,996 B2 | 8/2007 | Linnen et al. |
| 7,374,877 B2 | 5/2008 | Yang et al. |
| 7,425,417 B2 | 9/2008 | Bee et al. |
| 7,531,328 B2 | 5/2009 | Gerdes et al. |
| 7,666,600 B2 | 2/2010 | Linnen et al. |
| 7,723,040 B2 | 5/2010 | Bee et al. |
| 7,741,027 B2 | 6/2010 | Yang et al. |
| 7,851,148 B2 | 12/2010 | Han |
| 9,139,870 B2 | 9/2015 | Nelson et al. |
| 2005/0255517 A1 | 11/2005 | Gerdes et al. |
| 2006/0068380 A1 | 3/2006 | Schroder et al. |
| 2006/0141518 A1 | 6/2006 | Lao et al. |
| 2008/0131897 A1 | 6/2008 | Gerdes et al. |

FOREIGN PATENT DOCUMENTS

| | | |
|---|---|---|
| WO | 2008-055691 A1 | 5/2008 |
| WO | 2010-126913 A1 | 11/2010 |
| WO | 2011-003020 A | 1/2011 |

OTHER PUBLICATIONS

Murakami et al. (Nucleic Acids Research, 2009, 37(3):e19).*
International Preliminary Report on Patentability, International Application No. PCT/US2013/057458, dated Mar. 3, 2015.
International Search Report & Written Opinion, International Application No. PCT/US2013/057458, dated Dec. 16, 2013.
Thomson et al. "Molecular epidemiology of HIV-1 genetic forms and its significance for vaccine development and therapy," The Lancet, Infectious Diseases, Aug. 2002, pp. 461-471, vol. 2, Elsevier Limited, Oxford, UK.
AIPO Examination Report No. 1, Australian Application No. 2013308647, dated May 30, 2018.
SIPO First Office Action, Chinese Application No. 201380053605.0, dated Jan. 26, 2016.
SIPO Search Report, Chinese Application No. 201380053605.0, dated Jan. 26, 2016.
SIPO Second Office Action, Chinese Application No. 201380053605.0, dated Dec. 8, 2016.
SIPO Third Office Action, Chinese Application No. 201380053605.0, dated Aug. 24, 2017.
EPO Communication pursuant to Article 94(3) EPC, European Application No. 13760215.7, dated Oct. 20, 2017.
JPO Official Action, Japanese Application No. 2015-530085, dated Jun. 5, 2017.
JPO Official Action, Japanese Application No. 2015-530085, dated Apr. 25, 2018.
USPTO, Notice of Allowance, U.S. Appl. No. 14/014,607, dated May 18, 2015.
PCT International Preliminary Report on Patentability, International Application No. PCT/US2013/057458, dated Mar. 3, 2015.

\* cited by examiner

MULTIPHASE NUCLEIC ACID AMPLIFICATION

RELATED APPLICATIONS

This application is a divisional of U.S. application Ser. No. 14/014,607, filed Aug. 30, 2013, which claims the benefit of U.S. Provisional Application No. 61/695,106, filed Aug. 30, 2012; and U.S. Provisional Application No. 61/846,538, filed Jul. 15, 2013. The entire disclosures of these earlier applications are hereby incorporated by reference.

FIELD OF THE INVENTION

This invention generally relates to the field of molecular biology. More specifically, the invention relates to multiphase in vitro amplification of nucleic acids, which is useful for increasing the efficiency and precision of amplification in both uniplex and multiplex reactions, allowing a more sensitive detection of nucleic acid targets with improved quantitation characteristics as well as less interference between analytes in multiplex reactions.

BACKGROUND OF THE INVENTION

Nucleic acid amplification provides a means for generating multiple copies of a nucleic acid sequence that is relatively rare or unknown, for identifying the source of nucleic acids, or for making sufficient nucleic acid to provide a readily detectable amount. Amplification is useful in many applications, for example, in sequencing, diagnostics, drug development, forensic investigations, environmental analysis, and food testing. Many methods for amplifying nucleic acid sequences in vitro are known, including polymerase chain reaction (PCR), ligase chain reaction (LCR), replicase-mediated amplification, strand-displacement amplification (SDA), "rolling circle" types of amplification, and various transcription associated amplification methods. These known methods use different techniques to make amplified sequences, which usually are detected by using a variety of methods.

PCR amplification uses a DNA polymerase, oligonucleotide primers, and thermal cycling to synthesize multiple copies of both strands of a double-stranded DNA (dsDNA) or dsDNA made from a cDNA (U.S. Pat. Nos. 4,683,195, 4,683,202, and 4,800,159). LCR amplification uses an excess of two complementary pairs of single-stranded probes that hybridize to contiguous target sequences and are ligated to form fused probes complementary to the original target, which allows the fused probes to serve as a template for further fusions in multiple cycles of hybridization, ligation, and denaturation (U.S. Pat. No. 5,516,663 and EP 0320308 B1). Replicase-mediated amplification uses a self-replicating RNA sequence attached to the analyte sequence and a replicase, such as Qβ-replicase, to synthesize copies of the self-replicating sequence specific for the chosen replicase, such as a Qβ viral sequence (U.S. Pat. No. 4,786,600). The amplified sequence is detected as a substitute or reporter molecule for the analyte sequence. SDA uses a primer that contains a recognition site for a restriction endonuclease which allows the endonuclease to nick one strand of a hemi-modified dsDNA that includes the target sequence, followed by a series of primer extension and strand displacement steps (U.S. Pat. Nos. 5,422,252 and 5,547,861). Rolling circle types of amplification rely on a circular or concatenated nucleic acid structure that serves as a template used to enzymatically replicate multiple single-stranded copies from the template (e.g., U.S. Pat. Nos. 5,714,320 and 5,834,252). Transcription-associated amplification refers to methods that amplify a sequence by producing multiple transcripts from a nucleic acid template. Such methods generally use one or more oligonucleotides, of which one provides a promoter sequence, and enzymes with RNA polymerase and DNA polymerase activities to make a functional promoter sequence near the target sequence and then transcribe the target sequence from the promoter (e.g., U.S. Pat. Nos. 4,868,105, 5,124,246, 5,130,238, 5,399,491, 5,437,990, 5,554,516 and 7,374,885; and PCT Pub. No. WO 1988/010315).

Nucleic acid amplification methods may amplify a specific target sequence (e.g., a gene sequence), a group of related target sequences, or a surrogate sequence, which may be referred to as a tag sequence. This tag sequence can be used for a variety of purposes, such as detection, further amplification, as a binding tag for immobilization, as an adaptor for use in various functions in sequencing reactions, including next generation sequencing, etc. The tag sequence is functional for its intended purpose only if the analyte target sequence is present at some point during the reaction. Modified nucleic acid amplification methods may amplify more than one potential target sequence by using "universal" primer(s) or universal priming. One form of PCR amplification uses universal primers that bind to conserved sequences to amplify related sequences in a PCR reaction (Okamoto et al., 1992, *J. Gen. Virol.* 73:673-679, Persing et al., 1992, *J. Clin. Microbiol.* 30:2097-2103). Methods that use universal primers often are paired with use of a species-specific, gene-specific or type-specific primer or primers to generate an amplified sequence that is unique to a species, genetic variant, or viral type, which may be identified by sequencing or detecting some other characteristic of the amplified nucleic acid. Anchored PCR is another modified PCR method that uses a universal primer or an "adapter" primer to amplify a sequence that is only partially known. Anchored PCR introduces an "adaptor" or "universal" sequence into a cDNA and then uses a primer that binds to the introduced sequence in subsequent amplification steps. Generally, anchored-PCR uses a primer directed to a known sequence to make a cDNA, adds a known sequence (e.g., poly-G) to the cDNA or uses a common sequence in the cDNA (e.g., poly-T), and performs PCR by using a universal primer that binds to the added or common sequence in the cDNA and a downstream target-specific primer (Loh et al., 1989, *Science* 243:217-220; Lin et al., 1990, *Mol. Cell. Biol.* 10:1818-1821). Nested PCR may use primer(s) that contain a universal sequence unrelated to the analyte target sequence to amplify nucleic acid from unknown target sequences in a reaction (Sullivan et al., 1991, *Electrophoresis* 12:17-21; Sugimoto et al., 1991, *Agric. Biol. Chem.* 55:2687-2692).

Chamberlain et al. (*Nucleic Acid Res.*, 1988, 16:11141-11156) first demonstrated multiplex PCR analysis for the human dystrophin gene. Multiplex reactions are accomplished by careful selection and optimization of specific primers. Developing robust, sensitive and specific multiplex reactions have demanded a number of specific design considerations and empiric optimizations. This results in long development times and compromises reaction conditions that reduce assay sensitivity. In turn, development of new multiplex diagnostic tests becomes very costly. A number of specific problems have been identified that limit multiplex reactions. Incorporating primer sets for more than one target requires careful matching of the reaction efficiencies. If one primer amplifies its target with even slightly better efficiency, amplification becomes biased toward the more efficiently amplified target resulting in inefficient amplification, varied sensitivity and possible total failure of other target genes in the multiplex reaction. This is called "preferential amplification." Preferential amplification can sometimes be corrected by carefully matching all primer sequences to similar lengths and GC content and optimizing the primer concentrations, for example by increasing the primer concentration of the less efficient targets. Incorporation of inosine into primers in an attempt to adjust the primer amplification efficiencies also has been used (U.S. Pat. No. 5,738,995). Another approach is to design chimeric primers, where each primer contains a 3' region complementary to sequence-specific target recognition and a 5' region made up of a universal sequence. Using the universal sequence primer permits the amplification efficiencies of the different targets to be normalized (Shuber et al., *Genome Res.,* 1995, 5:488-493; and U.S. Pat. No. 5,882,856). Chimeric primers have also been utilized to multiplex isothermal strand displacement amplification (U.S. Pat. Nos. 5,422,252, 5,624, 825 and 5,736,365).

Since multiple primer sets are present in multiplex amplification reactions, multiplexing is frequently complicated by artifacts resulting from cross-reactivity of the primers. All possible combinations must be analyzed so that as the number of targets increases this becomes extremely complex and severely limits primer selection. Even carefully designed primer combinations often produce spurious products that result in either false negative or false positive results. The reaction kinetics and efficiency is altered when more than one reaction is occurring simultaneously. Each multiplexed reaction for each different specimen type must be optimized for $MgCl_2$ concentration and ratio to the deoxynucleotide concentration, KCl concentration, amplification enzyme concentration, and amplification reaction times and temperatures. There is a competition for the reagents in multiplex reactions so that all of the reactions plateau earlier. As a consequence, multiplexed reactions in general are less sensitive and often prone to more variability than the corresponding uniplex reaction.

Another consideration to simultaneous amplification reactions is that there must be a method for the discrimination and detection of each of the targets. The number of multiplexed targets is then further limited by the number of dye or other label moieties distinguishable within the reaction. As the number of different fluorescent moieties to be detected increases, so does the complexity of the optical system and data analysis programs necessary for result interpretation. One approach is to hybridize the amplified multiplex products to a solid phase then detect each target. This can utilize a planar hybridization platform with a defined pattern of capture probes (U.S. Pat. No. 5,955,268), or capture onto a bead set that can be sorted by flow cytometry (U.S. Pat. No. 5,981,180).

Due to the multitude of the technical issues discussed, current technology for multiplex gene detection is costly and severely limited in the number and combinations of genes that can be analyzed. Generally, these reactions multiplex only two or three targets with a maximum of around ten targets. Isothermal amplification reactions are more complex than PCR and even more difficult to multiplex (Van Deursen et al., *Nucleic Acid Res.,* 1999, 27:e15). U.S. Pat. No. 6,605,451 discloses a two-step PCR multiplex reaction where a small amount of each primer pair is added into a first PCR reaction mix, and a first exponential amplification is performed to increase the amount of target nucleic acids in the reaction. The first reaction is stopped mid log phase and is then separated into second reactions each containing primer pairs for one of the target nucleic acids. A full exponential amplification is then performed. Though a limited amount of each of the multiplex primer pairs is present in the first reaction, the above discussed problems common to multiplexing are still present. Further, these various primer pair species can all transfer into the secondary amplification reactions, causing common multiplex problems there as well.

Accordingly, there is still a need for a method which permits multiplexing of large numbers of targets without extensive design and optimization constraints, and which avoids problems common to multiplexing in the presence of a plurality of different amplification oligonucleotide pairs. In addition, there is an ongoing need to improve sensitivity and precision at the limit of detection and/or quantification for both multiplex and uniplex amplification reactions. The present invention addresses these and other needs.

SUMMARY OF THE INVENTION

As practiced in the art, all components required for nucleic acid amplification are present in the reaction mixture when amplification is started (herein referred to as the "single-phase method"). This single-phase method creates a problem in that undesired side reactions are usually initiated along with the desired amplification reaction. These side reactions often compete with and thus degrade the overall performance of the desired amplification reaction. Moreover, in multiplex amplification reactions, amplification of analytes that are present at higher amounts in the reaction mixture or analytes whose overall amplification efficiency is higher than that of other analytes unduly compete with and thus degrade the amplification of the other analytes in the mixture.

The improved method disclosed herein addresses these problems by conducting the amplification reaction in multiple phases. Using this method, the desired reaction or reactions are initiated and allowed to proceed to a certain level, whereas initiation or progression of other competing reactions is not supported by the reaction conditions. In this way, the desired reactions in essence get a head start on competing reactions, resulting in improved overall performance of the desired reactions. Furthermore, multiplex amplification reactions can be rendered less competitive with one another by conducting the overall amplification process in phases. Thus, similar to the situation described above, the lower efficiency reactions and/or those corresponding to lower initial levels of target analyte are allowed to proceed without the other reactions progressing unchecked and severely out-competing them. It is contemplated that the general principle of multiphase amplification is broadly applicable to a variety of amplification techniques and can be embodied in a wide variety of different modes, as described in more detail herein.

Accordingly, in the first aspect, the present invention provides a method for amplifying a target nucleic acid sequence in a sample including at least two steps. Initially, the target nucleic acid sequence is subjected to a first phase amplification reaction under conditions that do not support exponential amplification of the target nucleic acid sequence. The first phase amplification reaction generates a first amplification product, which is subsequently subjected to a second phase amplification reaction under conditions allowing exponential amplification of the first amplification product, thereby generating a second amplification product.

As noted above, in many cases, it is desirable to detect and quantify multiple target nucleic acid sequences in the same sample. Accordingly, in a second aspect, the present invention provides a method for amplifying a plurality of different target nucleic acid sequences in a sample including at least two steps. Initially, the target nucleic acid sequences are subjected to a first phase amplification reaction under conditions that do not support, or that prevent, exponential amplification of any of the target nucleic acid sequences. The first phase amplification reaction generates a plurality of first amplification products, which are subsequently subjected to a second phase amplification reaction under conditions allowing exponential amplification of the first amplification products, thereby generating a plurality of second amplification products.

In a modified version of the second aspect, the invention provides a method for amplifying a plurality of different target nucleic acid sequences in a sample, where some, but not all, of the target nucleic acid sequences are subjected to linear amplification, and/or some, but not all, of the target nucleic acid sequences are subjected to exponential amplification in at least one phase of the reaction. Accordingly, at least four possible variants of the first phase amplification are contemplated: (1) some of the target sequences are subjected to linear amplification, and the rest are left unamplified; (2) some of the target sequences are subjected to exponential amplification, and the rest are left unamplified; (3) some of the target sequences are subjected to linear amplification, some are subjected to exponential amplification and the rest are left unamplified; and (4) some of the target sequences are subjected to linear amplification and the rest are subjected to exponential amplification. Thus, in this aspect of the invention, the first phase amplification may result in amplification of all of the target nucleic acid sequences (option 4) or only a subset thereof (options 1-3). The subset of the target nucleic acid sequences may represent targets known to be present in relatively low quantities and/or targets that are difficult to amplify compared to other targets. The first phase amplification reaction generates one or more first amplification product(s). The first amplification product(s) and any unamplified target nucleic acid sequence(s) in the sample are then subjected to a second phase amplification reaction under conditions allowing exponential amplification thereof, generating a plurality of second amplification products. Alternatively, there can be more than two phases where conditions 1-4 above may apply for all phases except the final phase and where for the last phase any unamplified or linearly amplified target nucleic acid sequence(s) in the sample are subjected to an amplification reaction under conditions allowing exponential amplification thereof.

In a third aspect, the invention provides a composition for amplifying a target nucleic acid sequence in a sample. The composition includes the following components: (a) an amplification oligonucleotide that hybridizes to a first portion of the target nucleic acid sequence; (b) an optional target capture oligonucleotide that hybridizes to a second portion of the target nucleic acid sequence; and (c) an amplification enzyme. One of the key features of the present composition is that it lacks at least one component required for exponential amplification of the target nucleic acid sequence. As explained in detail elsewhere in this application, one of the advantages of the present composition is that it helps to reduce non-specific amplification, thereby focusing the amplification resources on the target sequence.

In a fourth aspect, the invention provides an alternative composition for amplifying a plurality of different target nucleic acid sequences in a sample. The composition includes the following components: (a) a plurality of different amplification oligonucleotide complexes that hybridize to a plurality of different target nucleic acid sequences, where each amplification oligonucleotide complex includes a first amplification oligonucleotide having a first target specific sequence that is joined to a second amplification oligonucleotide having a second target specific sequence; (b) a target capture oligonucleotide that hybridizes to a second portion of the target nucleic acid, and (c) an amplification enzyme. Once again, the composition lacks at least one component required for exponential amplification of the target nucleic acid sequences.

In a fifth aspect, the invention provides a method of quantifying a target nucleic acid sequence in a sample. In accordance with the method, first there is the step of (a) contacting the sample with a first amplification oligonucleotide, specific for a first portion of the target nucleic acid sequence, under conditions allowing hybridization of the first amplification oligonucleotide to the first portion of the target nucleic acid sequence, thereby generating a pre-amplification hybrid that includes the first amplification oligonucleotide and the target nucleic acid sequence. Next, there is the step of (b) isolating the pre-amplification hybrid by target capture onto a solid support followed by washing to remove any of the first amplification oligonucleotide that did not hybridize to the first portion of the target nucleic acid sequence in step (a). This is followed by the step of (c) amplifying, in a first phase amplification reaction mixture, at least a portion of the target nucleic acid sequence of the pre-amplification hybrid isolated in step (b) in a first phase, substantially isothermal, transcription-associated amplification reaction under conditions that support linear amplification thereof, but do not support exponential amplification thereof, thereby resulting in a reaction mixture including a first amplification product. Generally speaking, the first phase amplification reaction mixture includes a second amplification oligonucleotide, the second amplification oligonucleotide being complementary to a portion of an extension product of the first amplification oligonucleotide. As well, the first amplification product is not a template for nucleic acid synthesis during the first phase, substantially isothermal, transcription-associated amplification reaction. Next, there is the step of (d) combining the reaction mixture including the first amplification product with at least one component that participates in exponential amplification of the first amplification product, but that is lacking from the reaction mixture that includes the first amplification product, to produce a second phase amplification reaction mixture. Generally, the second phase amplification reaction mixture additionally includes a sequence-specific hybridization probe. Next, there is the step (e) of performing, in a second phase, substantially isothermal, transcription-associated amplification reaction in the second phase amplification reaction mixture, an exponential amplification of the first amplification product, thereby synthesizing a second amplification product. This is followed by the steps of (f) detecting, with the sequence-specific hybridization probe at regular time intervals, synthesis of the second amplification product in the second phase amplification reaction mixture; and then (g) quantifying the target nucleic acid sequence in the sample using results from the detecting step (f). In one generally preferred method, the first amplification oligonucleotide includes a 3' target specific sequence and a 5' promoter sequence for an RNA polymerase. In a preferred case, the RNA polymerase is T7 RNA polymerase. In another generally preferred method, the second amplification oligonucleotide is enzymatically extended in the first phase isothermal transcription-associated amplification reaction. In another generally preferred method, the solid support includes an immobilized capture probe. In another generally preferred method, step (a) further includes contacting the sample with a target capture oligonucleotide that hybridizes to the target nucleic acid sequence; and the pre-amplification hybrid includes the target nucleic acid sequence hybridized to each of the target capture oligonucleotide and the first amplification oligonucleotide. In another generally preferred method, the solid support includes magnetically attractable particles. In another generally preferred method, each of the first and second phase isothermal transcription-associated amplification reactions include an RNA polymerase and a reverse transcriptase, and the reverse transcriptase includes an endogenous RNaseH activity. In another generally preferred method, the at least one component includes the first amplification oligonucleotide. In another generally preferred method, the first amplification product of step (c) is a cDNA molecule with the same polarity as the target nucleic acid sequence in the sample, and the second amplification product of step (e) is an RNA molecule. In another generally preferred method, the sequence-specific hybridization probe in step (d) is a conformation-sensitive probe that produces a detectable signal when hybridized to the second amplification product. In another generally preferred method, the sequence-specific hybridization probe in step (d) is a fluorescently labeled sequence-specific hybridization probe. In another generally preferred method, step (g) includes quantifying the target nucleic acid sequence in the sample using a linear calibration curve and results from step (f). In another generally preferred method, step (c) includes amplifying by 10-fold to 10,000-fold, in the first phase amplification reaction mixture.

BRIEF DESCRIPTION OF THE DRAWINGS

In FIG. 3A, modified single-phase TMA as described above was used to amplify an HIV-1 target template. In FIG. 3B, the same HIV-1 template was amplified using the dual-phase TMA technique described in FIG. 1, i.e. the T7 primer was initially withheld from the amplification mixture and was provided in the second phase to start exponential amplification. FIG. 3C depicts calibration curve linear fits, showing significant shifts in sensitivity between the single-phase and dual-phase amplification reactions.

In FIG. 4A, the modified single-phase forward TMA was used to amplify an HIV-1 target template. In FIGS. 4B-4D, the T7 primer was withheld from the amplification mixture in phase 1, and different concentrations of T7 primer were provided in the second phase to initiate exponential amplification. Comparable significant shifts in sensitivity and robustness between the single-phase and dual-phase amplification reactions were observed at 1 pmol/rxn, 5 pmol/rxn and 10 pmol/rxn T7 primer.

In FIG. 5A, the modified single-phase forward TMA was used to amplify an HIV-1 target template. In FIGS. 5B-5D, T7 primer was withheld from the amplification mixture in phase 1 and was provided in the second phase to initiate exponential amplification. Comparable significant shifts in sensitivity and robustness between the single-phase and dual-phase amplification reactions were observed at 10 pmol/rxn and 15 pmol/rxn of non-T7 primer. The shift was somewhat less pronounced in the presence of 2 pmol/rxn non-T7 primer.

In FIG. 6A, the modified single-phase forward TMA was used to amplify an HIV-1 target template. As before, in FIGS. 6B-6C, the T7 primer was withheld from the amplification mixture in phase 1 and was provided in the second phase to initiate exponential amplification. In FIG. 6B, equal amounts of the enzyme reagent were added in the first and second phases of the amplification reaction. In FIG. 6C, the same total amount of the enzyme reagent was added in the first phase amplification, whereas no enzyme reagent was added in the second phase. Comparable significant shifts in sensitivity and robustness between the single-phase and dual-phase amplification reactions were observed in both experiments.

FIG. 7C depicts calibration curve linear fits, demonstrating a significant shift in sensitivity between the single-phase and dual-phase amplification reactions.

FIG. 8C depicts calibration curve linear fits, similarly showing a significant shift in sensitivity between the single-phase and dual-phase amplification reactions.

FIGS. 9A and 9B show detection of PCA3 in the presence of T2-ERG, whereas FIGS. 9D and 9E show detection of T2-ERG in the presence of PCA3. FIGS. 9C and 9F depict calibration curve linear fits, showing significant shifts in sensitivities between the single-phase and dual-phase amplification reactions for both targets in the duplex amplification context.

FIGS. 10A and 10B show detection of PCA3 in the presence of T2-ERG and PSA; FIGS. 10D and 10E show detection of T2-ERG in the presence of PCA3 and PSA; and FIGS. 10G and 10H show detection of PSA in the presence of PCA3 and T2-ERG. FIGS. 10C, 10F and 10I depict calibration curve linear fits, showing significant shifts in sensitivities between the single-phase and dual-phase amplification reactions for all three targets in the triplex amplification context.

In FIG. 11A, a modified single-phase reverse TMA was used to amplify a T2-ERG target template. In the modified single-phase reverse TMA, a non-T7 primer hybridizes to a target nucleic acid sequence during target capture, thereby eliminating the usual non-T7 primer annealing step at 60° C. following the target capture. Subsequently, a T7 primer is added along with additional non-T7 primer and all of the requisite amplification, detection and enzyme reagents, thus allowing exponential amplification to proceed. In FIG. 11B, the same T2-ERG template was amplified using a dual-phase reverse TMA protocol, where the non-T7 primer was withheld from the amplification mixture in phase 1 and was provided in the second phase to initiate exponential amplification. FIG. 11C depicts calibration curve linear fits, showing significant shifts in sensitivity between the single-phase and dual-phase amplification reactions.

FIGS. 12A, 12B and 12C show detection of T2-ERG in the presence of PCA3, PSA and CAP. In FIG. 12B, all four targets were subjected to the same dual-phase reverse TMA as the one described above in connection with FIG. 11B. In FIG. 12C, PCA3, PSA and CAP (or CAP alone) were subjected to linear amplification and T2-ERG was subjected to exponential amplification in the first phase of the reaction, and PCA3, PSA and CAP were subjected to exponential amplification and T2-ERG continued amplifying exponentially in the second phase (all of the amplification reactions proceeded in the same vessel).

FIGS. 13A, 13B and 13C show detection of T2-ERG in the presence of PCA3, PSA and CAP. In FIG. 13B, all four targets were subjected to the same dual-phase reverse TMA as the one described above in connection with FIG. 11B. In FIG. 13C, T2-ERG was subjected to linear amplification and the other 3 analytes were not amplified in phase 1, T2-ERG was subjected to exponential amplification and the 3 other analytes were not amplified in phase 2, and PCA3, PSA and CAP (or CAP alone) were subjected to exponential amplification and T2-ERG continued amplifying exponentially in phase 3 (all of the amplification reactions proceeded in the same vessel).

DETAILED DESCRIPTION OF THE INVENTION

Figure 1:
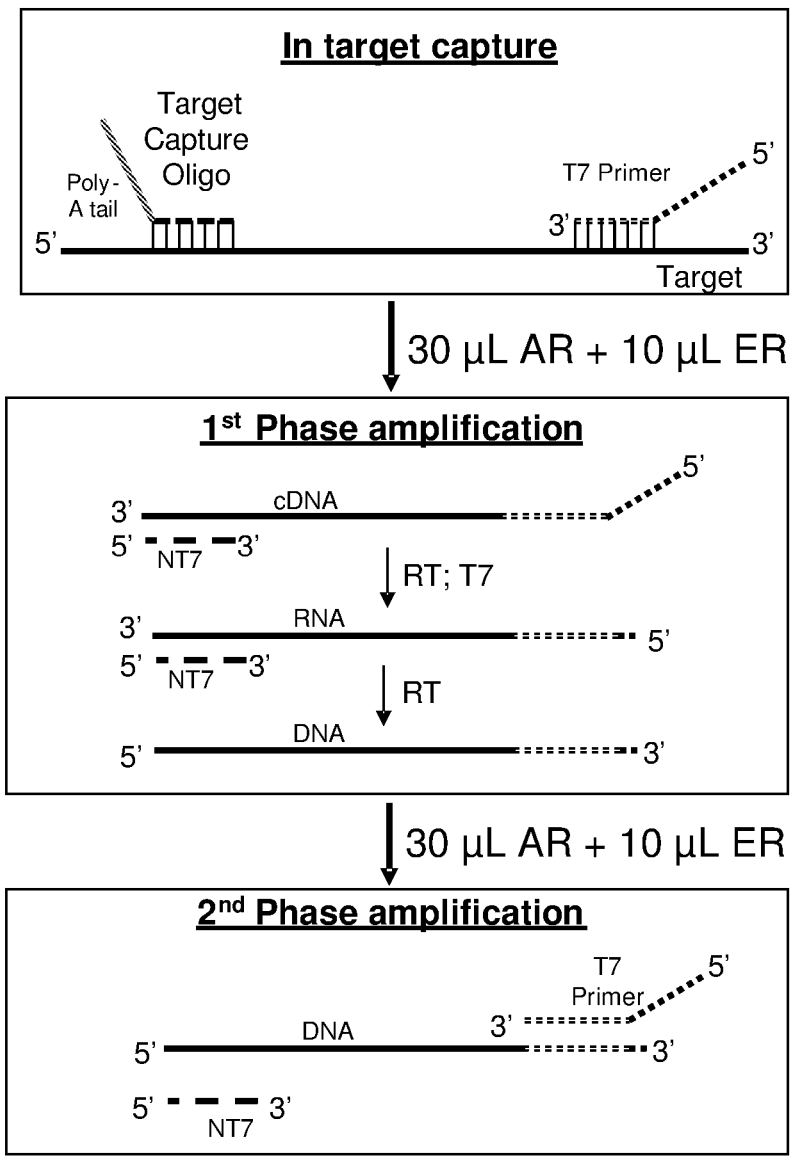
FIG. 1 illustrates an embodiment of dual-phase forward Transcription-Mediated Amplification (TMA). In this embodiment, an amplification primer containing a T7 promoter ("T7 primer") hybridizes to a target nucleic acid sequence during target capture, followed by removal of excess T7 primer. The amplification process is divided into at least two distinct phases. During the first phase, a non-T7 primer is introduced along with all of the requisite amplification and enzyme reagents (AR and ER, respectively), with the exception of additional T7 primer (RT: reverse transcriptase; T7: T7 RNA polymerase). In the presence of reverse transcriptase, the T7 primer hybridized to the target is extended, creating a cDNA copy, and the target RNA template is degraded by RNase H activity of RT. The non-T7 primer subsequently hybridizes to the cDNA and is then extended, filling in the promoter region of the T7 primer and creating an active, double-stranded template. The T7 polymerase then produces multiple RNA transcripts from the template. The non-T7 primer subsequently hybridizes to the RNA transcripts and is extended, producing promoterless cDNA copies of the target RNA template. The RNA strands are then degraded by RNase activity of RT. Because no T7 primer is available in the phase 1 amplification mixture, the reaction cannot proceed any further. The second phase is then started with the addition of T7 primer, thus initiating exponential amplification of the cDNA pool produced in phase 1.

For clarity of disclosure, and not by way of limitation, the detailed description of the invention is divided into the subsections that follow.

A. Definitions

Unless otherwise described, scientific and technical terms used herein have the same meaning as commonly understood by those skilled in the art of molecular biology based on technical literature, e.g., *Dictionary of Microbiology and Molecular Biology*, 2nd ed. (Singleton et al., 1994, John Wiley & Sons, New York, N.Y.), or other well-known technical publications related to molecular biology. Unless otherwise described, techniques employed or contemplated herein are standard methods well known in the art of molecular biology. To aid in understanding aspects of the disclosed methods and compositions, some terms are described in more detail or illustrated by embodiments described herein.

All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

Approximating language, as used herein throughout the specification and claims, may be applied to modify any quantitative or qualitative representation that could permissibly vary without resulting in a change in the basic function to which it is related. Accordingly, a value modified by a term such as "about" or "approximately" is not to be limited to the precise value specified, and may include values that differ from the specified value.

As used herein, the term "sample" refers to a specimen that may contain an analyte of interest, e.g., microbe, virus, nucleic acid such as a gene, or components thereof, which includes nucleic acid sequences in or derived from an analyte. Samples may be from any source, such as biological specimens or environmental sources. Biological specimens include any tissue or material derived from a living or dead organism that may contain an analyte or nucleic acid in or derived from an analyte. Examples of biological samples include respiratory tissue, exudates (e.g., bronchoalveolar lavage), biopsy, sputum, peripheral blood, plasma, serum, lymph node, gastrointestinal tissue, feces, urine, or other fluids, tissues or materials. Examples of environmental samples include water, ice, soil, slurries, debris, biofilms, airborne particles, and aerosols. Samples may be processed specimens or materials, such as obtained from treating a sample by using filtration, centrifugation, sedimentation, or adherence to a medium, such as matrix or support. Other processing of samples may include treatments to physically or mechanically disrupt tissue, cellular aggregates, or cells to release intracellular components that include nucleic acids into a solution which may contain other components, such as enzymes, buffers, salts, detergents and the like.

As used herein, the term "contacting" means bringing two or more components together. Contacting can be achieved by mixing all the components in a fluid or semi-fluid mixture. Contacting can also be achieved when one or more components are brought into physical contact with one or more other components on a solid surface such as a solid tissue section or a substrate.

As used herein, the term "nucleic acid" refers to a polynucleotide compound, which includes oligonucleotides, comprising nucleosides or nucleoside analogs that have nitrogenous heterocyclic bases or base analogs, covalently linked by standard phosphodiester bonds or other linkages. Nucleic acids include RNA, DNA, chimeric DNA-RNA polymers or analogs thereof. In a nucleic acid, the backbone may be made up of a variety of linkages, including one or more of sugar-phosphodiester linkages, peptide-nucleic acid (PNA) linkages (PCT Pub No. WO 95/32305), phosphorothioate linkages, methylphosphonate linkages, or combinations thereof. Sugar moieties in a nucleic acid may be ribose, deoxyribose, or similar compounds with substitutions, e.g., 2'methoxy and 2' halide (e.g., 2'-F) substitutions. Nitrogenous bases may be conventional bases (A, G, C, T, U), analogs thereof (e.g., inosine; *The Biochemistry of the Nucleic Acids* 5-36, Adams et al., ed., 11th ed., 1992), derivatives of purine or pyrimidine bases (e.g., N4-methyl deoxyguanosine, deaza- or aza-purines, deaza- or aza-pyrimidines, pyrimidines or purines with altered or replacement substituent groups at any of a variety of chemical positions, e.g., 2-amino-6-methylaminopurine, O6-methylguanine, 4-thio-pyrimidines, 4-amino-pyrimidines, 4-dimethylhydrazine-pyrimidines, and O4-alkyl-pyrimidines, or pyrazolo-compounds, such as unsubstituted or 3-substituted pyrazolo[3,4-d]pyrimidine (e.g., U.S. Pat. Nos. 5,378,825, 6,949,367 and PCT Pub. No. WO 93/13121)). Nucleic acids may include "abasic" positions in which the backbone does not have a nitrogenous base at one or more locations (U.S. Pat. No. 5,585,481), e.g., one or more abasic positions may form a linker region that joins separate oligonucleotide sequences together. A nucleic acid may comprise only conventional sugars, bases, and linkages as found in conventional RNA and DNA, or may include conventional components and substitutions (e.g., conventional bases linked by a 2'methoxy backbone, or a polymer containing a mixture of conventional bases and one or more analogs). The term includes "locked nucleic acids" (LNA), which contain one or more LNA nucleotide monomers with a bicyclic furanose unit locked in a RNA mimicking sugar conformation, which enhances hybridization affinity for complementary sequences in ssRNA, ssDNA, or dsDNA (Vester et al., 2004, *Biochemistry* 43(42): 13233-41).

As used herein, the interchangeable terms "oligonucleotide" and "oligomer" refer to nucleic acid polymers generally made of less than 1,000 nucleotide (nt), including those in a size range having a lower limit of about 2 to 5 nt and an upper limit of about 500 to 900 nt. Preferred oligonucleotides are in a size range having a 5 to 15 nt lower limit and a 50 to 500 nt upper limit, and particularly preferred embodiments are in a size range having a 10 to 20 nt lower limit and a 25 to 150 nt upper limit Preferred oligonucleotides are made synthetically by using any well-known in vitro chemical or enzymatic method, and may be purified after synthesis by using standard methods, e.g., high-performance liquid chromatography (HPLC). Representative oligonucleotides discussed herein include priming oligonucleotides (e.g., primers, nonT7 primers, T7 promoter-primers, etc.), promoter providers (which are promoter primers comprising a blocked 3'-end), detection probe oligonucleotides, target capture oligonucleotides, and blockers, to name a few. Priming oligonucleotides and promoter providers are generally referred to as "amplification oligonucleotides."

A "priming oligonucleotide" (or more simply, "primer") is an oligonucleotide, at least the 3'-end of which is complementary to a nucleic acid template, and which complexes (by hydrogen bonding or hybridization) with the template to give a primer:template complex suitable for initiation of synthesis by an RNA- or DNA-dependent DNA polymerase. A priming oligonucleotide is extended by the addition of covalently bonded nucleotide bases to its 3'-terminus, which bases are complementary to the template. The result is a primer extension product. A priming oligonucleotide of the present invention is typically at least 10 nucleotides in length, and may extend up to 15, 20, 25, 30, 35, 40, 50 or more nucleotides in length. Suitable and preferred priming oligonucleotides are described herein. Virtually all DNA polymerases (including reverse transcriptases) that are known require complexing of an oligonucleotide to a single-stranded template ("priming") to initiate DNA synthesis, whereas RNA replication and transcription (copying of RNA from DNA) generally do not require a primer. By its very nature of being extended by a DNA polymerase, a priming oligonucleotide does not comprise a 3'-blocking moiety.

As used herein, the term "amplification oligonucleotide complex" refers to two amplification oligonucleotides directly or indirectly joined together, as discussed below. Thus, an amplification oligonucleotide complex is made of a first amplification oligonucleotide and a second amplification oligonucleotide that are joined together.

A "tagged oligonucleotide" as used herein refers to an oligonucleotide that comprises at least a first region and a second region, where the first region comprises a "target hybridizing sequence" which hybridizes a target nucleic acid sequence of interest, and where the second region comprises a "tag sequence" situated 5' to the target hybridizing sequence and which does not stably hybridize or bind to a target nucleic acid containing the target nucleic acid sequence. Hybridization of the target hybridizing sequence to the target nucleic acid sequence produces a "tagged target nucleic acid sequence." The features and design considerations for the target hybridizing sequence component would be the same as for the priming oligonucleotides discussed herein. The "tag sequence" or "heterologous tag sequence" may be essentially any sequence provided that it does not stably hybridize to the target nucleic acid sequence of interest and, thereby, participate in detectable amplification of the native target (i.e., as would be found in a biological sample) prior to any sequence modification. The tag sequence preferably does not stably hybridize to any sequence derived from the genome of an organism being tested or, more particularly, to any target nucleic acid under reaction conditions. A tag sequence that is present in a tagged oligonucleotide is preferably designed so as not to substantially impair or interfere with the ability of the target hybridizing sequence to hybridize to its target sequence. Moreover, the tag sequence will be of sufficient length and composition such that once a complement of the tag sequence has been incorporated into an initial DNA primer extension product, a tag-specific priming oligonucleotide can then be used to participate in subsequent rounds of amplification as described herein. A tag sequence of the present invention is typically at least 10 nucleotides in length, and may extend up to 15, 20, 25, 30, 35, 40, 50 or more nucleotides in length. Skilled artisans will recognize that the design of tag sequences and tagged oligonucleotides for use in the present invention can follow any of a number of suitable strategies, while still achieving the objectives and advantages described herein. In certain embodiments, the tagged oligonucleotide is a "tagged priming oligonucleotide" comprising a tag sequence and a target hybridizing sequence. In other embodiments, the tagged oligonucleotide is a "tagged promoter oligonucleotide" comprising a tag sequence, a target hybridizing sequence and a promoter sequence situated 5' to the tag sequence and effective for initiating transcription therefrom. Exemplary tag sequences and methods of identifying particularly useful tag sequences are disclosed in commonly owned U.S. provisional patent application having Ser. No. 61/451,285. The disclosure of this provisional patent application is incorporated by reference.

Oligonucleotides that are not extended enzymatically include promoter provider oligonucleotides and blocker oligonucleotides. These oligonucleotides hybridize to a target nucleic acid, or its complement, but are not extended in a template-directed manner by enzymatic polymerase activity. To prevent enzymatic extension of an oligonucleotide, the 3'-terminus of the oligonucleotide can be chemically or structurally blocked using a blocking moiety, as is generally known in the art. Blocked oligonucleotides are described in, e.g., U.S. Pat. Nos. 5,399,491, 5,554,516, 5,824,518, and 7,374,885. A blocked oligonucleotide refers to an oligonucleotide that includes a chemical and/or structural modification that is usually near or at the 3' terminus and that prevents or impedes initiation of DNA synthesis from the oligonucleotide by enzymatic means. Examples of such modifications include use of a 3'2'-dideoxynucleotide base, a 3' non-nucleotide moiety that prevents enzymatic extension, or attachment of a short sequence in 3' to 5' orientation to the oligonucleotide to make a final oligonucleotide with two 5' termini (i.e., a first 5' to 3' oligonucleotide attached to a second, usually shorter, 5' to 3' oligonucleotide by covalently joining the oligonucleotides at their 3' termini) Another example of a modification is a "cap" made up of a sequence that is complementary to at least 3 nt at the 3'-end of the oligonucleotide such that the 5'-terminal base of the cap is complementary to the 3'-terminal base of the oligonucleotide. Although blocked oligonucleotides are not extended enzymatically, they may participate in nucleic acid amplification, for example by hybridizing to a specific location on a nucleic acid template strand to impede synthesis of a complementary strand beyond the position at which the blocked oligonucleotide is bound.

Sizes of the amplification oligonucleotides are generally determined by the function portions that are included in the oligonucleotide. Component portions of a promoter primer or promoter provider oligonucleotide include a promoter sequence specific for an RNA polymerase (RNP). RNP and their corresponding promoter sequences are well known and may be purified from or made synthetically in vitro by using materials derived from a variety of sources, e.g., viruses, bacteriophages, fungi, yeast, bacteria, animal, plant or human cells. Examples of RNP and promoters include RNA polymerase III and its promoter (U.S. Pat. No. 7,241,618), bacteriophage T7 RNA polymerase and its promoter or mutants thereof (U.S. Pat. Nos. 7,229,765 and 7,078,170), RNA polymerase and promoter from *Thermus thermophilus* (U.S. Pat. No. 7,186,525), RNA polymerases from HIV-1 or HCV, and plant directed RNPs (U.S. Pat. No. 7,060,813). A promoter primer or provider oligonucleotide includes a promoter sequence that is linked functionally to the chosen RNP. Preferred embodiments of promoter primer or promoter provider oligonucleotides include a T7 promoter sequence that is used with T7 RNP, where the promoter sequence is in the range of 25 to 30 nt, such as a promoter sequence of SEQ ID NO:1 (AATTTAATACGACTCACTATAGGGAGA) or SEQ ID NO:2 (GAAATTAATACGACTCACTATAGGGAGA).

Amplification oligonucleotides that include a tag portion typically include a tag sequence in a range of 5 to 40 nt, with preferred embodiments in a range of 10 to 25 nt, or 10 to 30 nt, or 15 to 30 nt. Amplification oligonucleotides that include a target specific (TS) portion typically include a TS sequence in a range of 10 to 45 nt, with preferred embodiments in a range of 10 to 35 nt or 20 to 30 nt. Amplification oligonucleotides that include multiple tag sequences and/or multiple TS sequences and/or a promoter sequence will be in a size range that is determined by the length of its individual functional sequences. For example, a promoter primer or provider oligonucleotide that includes a tag sequence and a TS sequence will be the sum of the sizes of the promoter, tag and TS sequences, and may optionally include linking nucleotides or non-nucleotide portions (e.g., abasic linkers). Amplification oligonucleotides made up of multiple functional components as described herein may be covalently linked by standard phosphodiester linkages, nucleic acid analog linkages, or non-nucleic acid linkages directly between the different functional portions or may be non-covalently linked together by using additional nucleic acid sequences or non-nucleic (e.g., abasic linkages) compounds that serve as spacers and/or linkages between functional portions. Some embodiments of amplification oligonucleotides may be linked together to form a complex by using non-covalent linkages, such as by using interactions of binding pair members between the oligonucleotides, which includes direct hybridization of complementary sequences contained in two or more oligonucleotides, or via a linking component (including one or more additional oligonucleotides) to which the individual binding pair members of an oligonucleotide complex bind.

As used herein, "amplification" of a target nucleic acid refers to the process of creating in vitro nucleic acid strands that are identical or complementary to at least a portion of a target nucleic acid sequence, or a universal or tag sequence that serves as a surrogate for the target nucleic acid sequence, all of which are only made if the target nucleic acid is present in a sample. Typically, nucleic acid amplification uses one or more nucleic acid polymerase and/or transcriptase enzymes to produce multiple copies of a target polynucleotide or fragments thereof, or of a sequence complementary to the target polynucleotide or fragments thereof, or of a universal or tag sequence that has been introduced into the amplification system to serve as a surrogate for the target polynucleotide, such as in a detection step, to indicate the presence of the target polynucleotide at some point in the assay, or as a site for further priming in an amplification reaction, or for use in a sequencing-related workflow or sequencing reaction. In vitro nucleic acid amplification techniques are well known and include transcription-associated amplification methods, such as Transcription-Mediated Amplification (TMA) or Nucleic Acid Sequence-Based Amplification (NASBA), and other methods such as Polymerase Chain Reaction (PCR), Reverse Transcriptase-PCR (RT-PCR), Replicase Mediated Amplification, and Ligase Chain Reaction (LCR).

As used herein, the term "linear amplification" refers to an amplification mechanism that is designed to produce an increase in the target nucleic acid linearly proportional to the amount of target nucleic acid in the reaction. For instance, multiple RNA copies can be made from a DNA target using a transcription-associated reaction, where the increase in the number of copies can be described by a linear factor (e.g., starting copies of template×100). In preferred embodiments, a first phase linear amplification in a multiphase amplification procedure increases the starting number of target nucleic acid strands or the complements thereof by at least 10 fold, more preferably 100 fold, or still more preferably by 10 to 1,000 fold before the second phase amplification reaction is begun. An example of a linear amplification system is "T7-based Linear Amplification of DNA" (TLAD; see Liu et al., *BMC Genomics*, 4: Art. No. 19, May 9, 2003). Other methods are disclosed herein. Accordingly, the term "linear amplification" refers to an amplification reaction which does not result in the exponential amplification of a target nucleic acid sequence. The term "linear amplification" does not refer to a method that simply makes a single copy of a nucleic acid strand, such as the transcription of an RNA molecule into a single cDNA molecule as in the case of reverse transcription (RT)-PCR.

As used herein, the term "exponential amplification" refers to nucleic acid amplification that is designed to produce an increase in the target nucleic acid geometrically proportional to the amount of target nucleic acid in the reaction. For example, PCR produces one DNA strand for every original target strand and for every synthesized strand present. Similarly, transcription-associated amplification produces multiple RNA transcripts for every original target strand and for every subsequently synthesized strand. The amplification is exponential because the synthesized strands are used as templates in subsequent rounds of amplification. An amplification reaction need not actually produce exponentially increasing amounts of nucleic acid to be considered exponential amplification, so long as the amplification reaction is designed to produce such increases.

As used herein, the term "substantially isothermal amplification" refers to an amplification reaction that is conducted at a substantially constant temperature. The isothermal portion of the reaction may be preceded or followed by one or more steps at a variable temperature, for example, a first denaturation step and a final heat inactivation step or cooling step. It will be understood that this definition by no means excludes certain, preferably small, variations in temperature but is rather used to differentiate the isothermal amplification techniques from other amplification techniques known in the art that basically rely on "cycling temperatures" in order to generate the amplified products. Isothermal amplification differs from PCR, for example, in that the latter relies on cycles of denaturation by heating followed by primer hybridization and polymerization at a lower temperature.

Preferred embodiments of the disclosed methods use aspects of isothermal amplification systems that are generally referred to as "transcription-associated amplification" methods, which amplify a target sequence by producing multiple transcripts from a nucleic acid template. Such methods generally use one or more oligonucleotides, of which one provides a promoter sequence, deoxyribonucleoside triphosphates (dNTPs), ribonucleoside triphosphates (rNTPs), and enzymes with RNA polymerase and DNA polymerase activities to generate a functional promoter sequence near the target sequence and then transcribe the target sequence from the promoter (e.g., U.S. Pat. Nos. 4,868,105, 5,124,246, 5,130,238, 5,399,491, 5,437,990, 5,554,516 and 7,374,885; and PCT Pub. Nos. WO 1988/001302, WO 1988/010315 and WO 1995/003430). Examples include Transcription-Mediated Amplification (TMA), nucleic acid sequence based amplification (NASBA) and Self-Sustained Sequence Replication (3SR). Although the disclosed preferred embodiments rely on TMA (U.S. Pat. Nos. 5,399,491 and 5,554,516) or one-primer transcription-associated amplification (U.S. Pat. Nos. 7,374,885, 7,696,337 and 7,939,260), a person of ordinary skill in the art will appreciate that alternative amplification methods based on polymerase mediated extension of oligonucleotide sequences may also be used with the compositions and/or method steps described herein.

To aid in understanding of some of the embodiments disclosed herein, the TMA method that has been described in detail previously (e.g., U.S. Pat. Nos. 5,399,491, 5,554,516 and 5,824,518) is briefly summarized. In TMA, a target nucleic acid that contains the sequence to be amplified is provided as single stranded nucleic acid (e.g., ssRNA or ssDNA). Any conventional method of converting a double stranded nucleic acid (e.g., dsDNA) to a single-stranded nucleic acid may be used. A promoter primer binds specifically to the target nucleic acid at its target sequence and a reverse transcriptase (RT) extends the 3' end of the promoter primer using the target strand as a template to create a cDNA copy, resulting in a RNA:cDNA duplex. RNase activity (e.g., RNase H of RT enzyme) digests the RNA of the RNA:cDNA duplex and a second primer binds specifically to its target sequence in the cDNA, downstream from the promoter-primer end. Then RT synthesizes a new DNA strand by extending the 3' end of the second primer using the cDNA as a template to create a dsDNA that contains a functional promoter sequence. RNA polymerase specific for the functional promoter initiates transcription to produce about 100 to 1000 RNA transcripts (amplified copies or amplicons) complementary to the initial target strand. The second primer binds specifically to its target sequence in each amplicon and RT creates a cDNA from the amplicon RNA template to produce a RNA:cDNA duplex. RNase digests the amplicon RNA from the RNA:cDNA duplex and the target-specific sequence of the promoter primer binds to its complementary sequence in the newly synthesized DNA and RT extends the 3' end of the promoter primer as well as the 3' end of the cDNA to create a dsDNA that contains a functional promoter to which the RNA polymerase binds and transcribes additional amplicons that are complementary to the target strand. Autocatalytic cycles that use these steps repeatedly during the reaction produce about a billion-fold amplification of the initial target sequence. Amplicons may be detected during amplification (real-time detection) or at an end point of the reaction (end-point detection) by using a probe that binds specifically to a sequence contained in the amplicons. Detection of a signal resulting from the bound probes indicates the presence of the target nucleic acid in the sample.

Another form of transcription associated amplification that uses a single primer and one or more additional amplification oligonucleotides to amplify nucleic acids in vitro by making transcripts that indicate the presence of the target nucleic acid has been described in detail previously (U.S. Pat. Nos. 7,374,885, 7,696,337 and 7,939,260). Briefly, this single-primer method uses a priming oligonucleotide, a promoter oligonucleotide (or promoter provider oligonucleotide) that is modified to prevent the initiation of DNA synthesis from its 3' end and, optionally, a blocker molecule (e.g., a 3'-blocked oligonucleotide) to terminate elongation of a cDNA from the target strand. The method synthesizes multiple copies of a target sequence by treating a target nucleic acid that includes a RNA target sequence with (i) a priming oligonucleotide which hybridizes to the 3'-end of the target sequence such that a primer extension reaction can be initiated therefrom and (ii) a blocker molecule that binds to the target nucleic acid adjacent to or near the 5'-end of the target sequence. The priming oligonucleotide is extended in a primer extension reaction by using a DNA polymerase to give a DNA primer extension product complementary to the target sequence, in which the DNA primer extension product has a 3' end determined by the blocker molecule and which is complementary to the 5'-end of the target sequence. The method then separates the DNA primer extension product from the target sequence by using an enzyme which selectively degrades the target sequence and treats the DNA primer extension product with a promoter oligonucleotide made up of a first region that hybridizes to a 3'-region of the DNA primer extension product to form a promoter oligonucleotide:DNA primer extension product hybrid, and a second region that is a promoter for an RNA polymerase which is situated 5' to the first region, where the promoter oligonucleotide is modified to prevent the initiation of DNA synthesis from the promoter oligonucleotide. The method extends the 3'-end of the DNA primer extension product in the promoter oligonucleotide:DNA primer extension product hybrid to add a sequence complementary to the second region of the promoter oligonucleotide, which is used to transcribe multiple RNA products complementary to the DNA primer extension product using an RNA polymerase which recognizes the promoter and initiates transcription therefrom. This method produces RNA transcripts that are substantially identical to the target sequence.

An embodiment of the one-primer Transcription-Mediated Amplification method synthesizes multiple copies of an RNA target sequence by hybridizing to the target RNA a primer at a location in the 3' portion of the target sequence and a 3' blocked oligonucleotide (i.e., the blocker oligonucleotide) at a location in the 5' portion of the target sequence. Then the DNA polymerase activity of RT initiates extensions from the 3' end of the primer to produce a cDNA in a duplex with the template strand (a RNA:cDNA duplex). The 3' blocked oligonucleotide binds to the target strand at a position adjacent to the intended 5' end of the sequence to be amplified because the bound 3' blocked oligonucleotide impedes extension of the cDNA beyond that location. That is, the 3' end of the cDNA is determined by the position of the blocker molecule because polymerization stops when the extension product reaches the blocking molecule bound to the target strand. The RNA:cDNA duplex is separated by RNAse activity (RNase H of RT) that degrades the RNA, although those skilled in the art will appreciate that any form of strand separation may be used. A promoter provider oligonucleotide includes a 5' promoter sequence for an RNA polymerase and a 3' sequence complementary to a sequence in the 3' region of the cDNA to which it hybridizes. The promoter provider oligonucleotide has a modified 3' end that includes a blocking moiety to prevent initiation of DNA synthesis from the 3' end of the promoter provider oligonucleotide. In the duplex made of the promoter provider hybridized to the cDNA, the 3'-end of the cDNA is extended by using DNA polymerase activity of RT and the promoter provider oligonucleotide serves as a template to add a promoter sequence to the 3' end of the cDNA, which creates a functional double-stranded promoter made up of the sequence on the promoter provider oligonucleotide and the complementary cDNA sequence made from the promoter provider template. RNA polymerase specific for the promoter sequence binds to the functional promoter and transcribes multiple RNA transcripts that are complementary to the cDNA and substantially identical to the target sequence of the initial target RNA strand. The resulting amplified RNA can cycle through the process again by binding the primer and serving as a template for further cDNA production, ultimately producing many amplicons from the initial target nucleic acid present in the sample. Embodiments of the single primer transcription associated amplification method do not require use of the 3' blocked oligonucleotide that serves as a blocker molecule and, if a binding molecule is not included the cDNA product made from the primer has an indeterminate 3' end, but amplification proceeds substantially the same as described above. Due to the nature of this amplification method, it is performed under substantially isothermal conditions, i.e., without cycles of raising and lowering incubation temperatures to separate strands or allow hybridization of primers as is used in PCR-based methods.

As used herein, the term "tag" refers to a nucleotide sequence covalently attached to a target-specific sequence of an oligonucleotide for the purpose of conferring some additional functionality beyond binding to the target sequence. Non-limiting examples of oligonucleotide tags include a 5' promoter for an RNA polymerase, a primer binding site, a sequencing tag, a mass tag, a bar code tag, a capture tag, and so forth (e.g., U.S. Pat. Nos. 5,422,252, 5,882,856, 6,828,098, and PCT Pub. No. 05/019479). An oligonucleotide tag can be unique to each target sequence or universal (shared by a plurality of target sequences, e.g., U.S. Pat. No. 5,104,792), depending on the specifics of a particular assay.

As used herein, "detection" of the amplified products may be accomplished by using any known method. For example, the amplified nucleic acids may be associated with a surface that results in a detectable physical change (e.g., an electrical change). Amplified nucleic acids may be detected in solution phase or by concentrating them in or on a matrix and detecting labels associated with them (e.g., an intercalating agent such as ethidium bromide or cyber green). Other detection methods use probes complementary to a sequence in the amplified product and detect the presence of the probe:product complex, or use a complex of probes to amplify the signal detected from amplified products (e.g., U.S. Pat. Nos. 5,424,413, 5,451,503 and 5,849,481). Other detection methods use a probe in which signal production is linked to the presence of the target sequence because a change in signal results only when the labeled probe binds to amplified product, such as in a molecular beacon, molecular torch, or hybridization switch probe (e.g., U.S. Pat. Nos. 5,118,801, 5,312,728, 5,925,517, 6,150,097, 6,361,945, 6,534,274, 6,835,542, 6,849,412 and 8,034,554; and U.S. Pub. No. 2006/0194240 A1). Such probes typically use a label (e.g., fluorophore) attached to one end of the probe and an interacting compound (e.g., quencher) attached to another location of the probe to inhibit signal production from the label when the probe is in one conformation ("closed") that indicates it is not hybridized to amplified product, but a detectable signal is produced when the probe is hybridized to the amplified product which changes its conformation (to "open"). Detection of a signal from directly or indirectly labeled probes that specifically associate with the amplified product indicates the presence of the target nucleic acid that was amplified.

As used herein, the term "label" refers to a molecular moiety or compound that can be detected or lead to a detectable response, which may be joined directly or indirectly to a nucleic acid probe. Direct labeling may use bonds or interactions to link label and probe, which includes covalent bonds, non-covalent interactions (hydrogen bonds, hydrophobic and ionic interactions), or chelates or coordination complexes. Indirect labeling may use a bridging moiety or linker (e.g. antibody, oligonucleotide, or other compound), which is directly or indirectly labeled, which may amplify a signal. Labels include any detectable moiety. Examples of useful detectable moieties include radionuclides, ligands such as biotin or avidin, enzymes, enzyme substrates, reactive groups, chromophores (detectable dyes, particles, or beads), fluorophores, or luminescent compounds (e.g., bioluminescent, phosphorescent, or chemiluminescent label). Preferred chemiluminescent labels include acridinium ester ("AE") and derivatives thereof (U.S. Pat. Nos. 5,639,604, 5,656,207 and 5,658,737). Preferred labels are detectable in a homogeneous assay in which bound labeled probe in a mixture exhibits a detectable change compared to that of unbound labeled probe, e.g., stability or differential degradation, without requiring physical separation of bound from unbound forms (e.g., U.S. Pat. Nos. 5,283,174, 5,656,207 and 5,658,737). Methods of synthesizing labels, attaching labels to nucleic acids, and detecting labels are well known (e.g., Sambrook et al., *Molecular Cloning, A Laboratory Manual,* 2nd ed. (Cold Spring Harbor Laboratory Press, Cold Spring Harbor, N.Y., 1989), Chapter 10; U.S. Pat. Nos. 4,581,333, 5,283,174, 5,547,842, 5,656,207 and 5,658,737).

Members of a specific binding pair (or binding partners) are moieties that specifically recognize and bind to each other. Members may be referred to as a first binding pair member (BPM1) and second binding pair member (BPM2), which represent a variety of moieties that specifically bind together. Specific binding pairs are exemplified by a receptor and its ligand, enzyme and its substrate, cofactor or coenzyme, an antibody or Fab fragment and its antigen or ligand, a sugar and lectin, biotin and streptavidin or avidin, a ligand and chelating agent, a protein or amino acid and its specific binding metal such as histidine and nickel, substantially complementary polynucleotide sequences, which include completely or partially complementary sequences, and complementary homopolymeric sequences. Specific binding pairs may be naturally occurring (e.g., enzyme and substrate), synthetic (e.g., synthetic receptor and synthetic ligand), or a combination of a naturally occurring BPM and a synthetic BPM.

As used herein, the term "target capture" refers to selectively separating a target nucleic acid from other components of a sample mixture, such as cellular fragments, organelles, proteins, lipids, carbohydrates, or other nucleic acids. A target capture system may be specific and selectively separate a predetermined target nucleic acid from other sample components (e.g., by using a sequence specific to the intended target nucleic acid), or it may be nonspecific and selectively separate a target nucleic acid from other sample components by using other characteristics of the target (e.g., a physical trait of the target nucleic acid that distinguishes it from other sample components which do not exhibit that physical characteristic). Preferred target capture methods and compositions have been previously described in detail (U.S. Pat. Nos. 6,110,678 and 6,534,273; and US Pub. No. 2008/0286775 A1). Preferred target capture embodiments use a target capture oligonucleotide in solution phase and an immobilized capture probe attached to a support to form a complex with the target nucleic acid and separate the captured target from other components.

As used herein, the term "target capture oligonucleotide" refers to at least one nucleic acid oligonucleotide that bridges or joins a target nucleic acid and an immobilized capture probe by using binding pair members, such as complementary nucleic acid sequences or biotin and streptavidin. In one approach, the target capture oligonucleotide binds nonspecifically to the target nucleic acid and immobilizes it to a solid support. In a different approach, a target specific (TS) sequence of the target capture oligonucleotide binds specifically to a sequence in the target nucleic acid. In both approaches the target capture oligonucleotide includes an immobilized capture probe-binding region that binds to an immobilized capture probe (e.g., by specific binding pair interaction). In embodiments in which the TS sequence and the immobilized capture probe-binding region are both nucleic acid sequences, they may be covalently joined to each other, or may be on different oligonucleotides joined by one or more linkers.

An "immobilized capture probe" provides a means for joining a target capture oligonucleotide to a solid support. The immobilized capture probe is a base sequence recognition molecule joined to the solid support, which facilitates separation of bound target polynucleotide from unbound material. Any known solid support may be used, such as matrices and particles free in solution. For example, solid supports may be nitrocellulose, nylon, glass, polyacrylate, mixed polymers, polystyrene, silane polypropylene and, preferably, magnetically attractable particles. Particularly preferred supports include magnetic spheres that are monodisperse (i.e., uniform in size±about 5%), thereby providing consistent results, which is particularly advantageous for use in an automated assay. The immobilized capture probe may be joined directly (e.g., via a covalent linkage or ionic interaction), or indirectly to the solid support. Common examples of useful solid supports include magnetic particles or beads.

As used herein, the term "separating" or "purifying" generally refers to removal of one or more components of a mixture, such as a sample, from one or more other components in the mixture. Sample components include nucleic acids in a generally aqueous solution phase, which may include cellular fragments, proteins, carbohydrates, lipids, and other compounds. Preferred embodiments separate or remove at least 70% to 80%, and more preferably about 95%, of the target nucleic acid from other components in the mixture.

B. Methods of Multiphase Amplification

As noted above, the first aspect of the present invention is concerned with a method for amplifying a target nucleic acid sequence in a sample including the following steps. Initially, the target nucleic acid sequence is subjected to a first phase amplification reaction under conditions that do not support exponential amplification of the target nucleic acid sequence. The first phase amplification reaction generates a first amplification product, which is subsequently subjected to a second phase amplification reaction under conditions allowing exponential amplification of the first amplification product, thereby generating a second amplification product.

In this aspect, the target nucleic acid sequence may be any RNA or DNA sequence; however, in preferred embodiments, the target sequence is an RNA sequence. In some embodiments, before the first amplification step, the sample may be contacted with a first amplification oligonucleotide under conditions allowing hybridization of the first amplification oligonucleotide to a portion of the target nucleic acid sequence in the sample. The first amplification oligonucleotide usually includes a target specific sequence and optionally, one or more tag sequences. In preferred embodiments, the tag sequence may be a 5' promoter sequence recognized by an RNA polymerase, such as T7 RNA polymerase, an amplification primer binding site, a specific binding site used for capture, or a sequencing primer binding site. In some embodiments, a second amplification oligonucleotide may be used in combination with the first amplification oligonucleotide before the first amplification step.

In many cases, it may be desirable to isolate the target nucleic acid sequence prior to the first phase amplification. To this end, the sample may be contacted with a target capture oligonucleotide under conditions allowing hybridization of the target capture oligonucleotide to a portion of the target nucleic acid sequence. In some embodiments, the target nucleic acid is captured onto the solid support directly, for example by interaction with an immobilized capture probe. Alternatively, the target nucleic acid is captured onto the solid support as a member of a three molecule complex, with the target capture oligonucleotide bridging the target nucleic acid and the immobilized capture probe. In either scenario, the solid support typically includes a plurality of magnetic or magnetizable particles or beads that can be manipulated using a magnetic field. Preferably, the step of isolating the target nucleic acid sequence also includes washing the target capture oligonucleotide:target nucleic acid sequence hybrid to remove undesired components that may interfere with subsequent amplification.

The step of isolating the target nucleic acid sequence may sometimes include contacting the sample with a first amplification oligonucleotide under conditions allowing hybridization of the first amplification oligonucleotide to a portion of the target nucleic acid sequence. In some embodiments, the portion of the target sequence targeted by the first amplification oligonucleotide may be completely different (e.g. non-overlapping) from the portion targeted by the target capture oligonucleotide. Alternatively, the portion of the target sequence targeted by the first amplification oligonucleotide may fully or partially overlap with, or even be identical to, the portion targeted by the target capture oligonucleotide. The first amplification oligonucleotide usually includes a target specific sequence and optionally, one or more tag sequence(s). In preferred embodiments, the tag sequence may be a 5' promoter sequence recognized by an RNA polymerase, such as T7 RNA polymerase, and other functional sites as described above. In some embodiments, a second amplification oligonucleotide may be used in combination with the first amplification oligonucleotide during the target nucleic acid sequence isolation step. It is contemplated that the first and second amplification oligonucleotides may form a complex, e.g., a direct hybrid (DH) complex. In some embodiments, at least one of the first and second amplification oligonucleotides may include a tag sequence (e.g., a universal tag) located 5' to a target specific sequence, which tag sequence may be targeted by an amplification oligonucleotide during the second phase amplification.

The amplification oligonucleotide primers are often provided in a target capture reagent. In certain preferred embodiments, the target capture reagent includes only one of the amplification oligonucleotides to be used in the production of a particular amplification product in a first phase amplification reaction. The amplification oligonucleotides can be hybridized to a target nucleic acid, and isolated along with the target sequence during the target capture step. One advantage of this method is that by hybridizing the amplification oligonucleotide to the target nucleic acid during target capture, the captured nucleic acids can be washed to remove sample components, such as unhybridized amplification oligonucleotide primers, providers, and/or complexes. In a multiplex reaction, removing unhybridized amplification oligonucleotides allows the multiplex amplification reaction to occur without interference from the excess amplification oligonucleotides, thereby substantially reducing or eliminating the problems common to multiplex reactions. Further, if the amplification oligonucleotide or amplification oligonucleotide complex comprises a tag sequence, then the tag is incorporated into the first amplification product, thereby allowing for subsequent amplification using primers specific for the tag sequence.

As noted above, the first phase amplification reaction is carried out under conditions that do not support exponential amplification of the target nucleic acid sequence. In preferred embodiments, the first phase amplification reaction is a linear amplification reaction. The first phase amplification reaction will typically produce from about 2-fold to about 10,000-fold amplification, and preferably from about 10-fold to about 10,000-fold amplification, of the target nucleic acid sequence. In some embodiments, the first phase amplification reaction is substantially isothermal, i.e., it does not involve thermal cycling characteristic of PCR and other popular amplification techniques. Typically, the first phase amplification reaction will involve contacting the target nucleic acid sequence with a first phase amplification reaction mixture that supports linear amplification of the target nucleic acid sequence and lacks at least one component that is required for its exponential amplification. In some embodiments, the first phase amplification reaction mixture includes an amplification enzyme selected from a reverse transcriptase, a polymerase, and a combination thereof. The polymerase is typically selected from an RNA-dependent DNA polymerase, a DNA-dependent DNA polymerase, a DNA-dependent RNA polymerase, and a combination thereof. In preferred embodiments, the first phase amplification reaction mixture further includes a ribonuclease (RNase), such as an RNase H or a reverse transcriptase with an RNase H activity. Preferably, the first phase amplification mixture includes a reverse transcriptase with an RNase H activity and an RNA polymerase.

In some embodiments, the first phase amplification mixture may also include an amplification oligonucleotide. Preferably, the amplification oligonucleotide includes a 5' promoter sequence for an RNA polymerase, such as T7 RNA polymerase, and/or a blocked 3' terminus that prevents its enzymatic extension. In addition, the first phase amplification mixture may sometimes include a blocker oligonucleotide to prevent enzymatic extension of the target nucleic sequence beyond a desired end-point.

As noted above, the key feature of the first phase amplification reaction is its inability to support an exponential amplification reaction because one or more components required for exponential amplification are lacking, and/or an agent is present which inhibits exponential amplification, and/or the temperature of the reaction mixture is not conducive to exponential amplification, etc. Without limitation, the lacking component required for exponential amplification and/or inhibitor and/or reaction condition may be selected from the following group: an amplification oligonucleotide (e.g., an amplification oligonucleotide comprising a 5' promoter sequence for an RNA polymerase, a non-promoter amplification oligonucleotide, or a combination thereof), an enzyme (e.g., a polymerase, such as an RNA polymerase), a nuclease (e.g., an exonuclease, an endonuclease, a cleavase, an RNase, a phosphorylase, a glycosylase, etc), an enzyme co-factor, a chelator (e.g., EDTA or EGTA), ribonucleotide triphosphates (rNTPs), deoxyribonucleotide triphosphates (dNTPs), $Mg^{2+}$, a salt, a buffer, an enzyme inhibitor, a blocking oligonucleotide, pH, temperature, salt concentration and a combination thereof. In some cases, the lacking component may be involved indirectly, such as an agent that reverses the effects of an inhibitor of exponential amplification which is present in the first phase reaction.

As noted above, the second phase (or later, if there are more than 2 phases) amplification reaction is carried out under conditions that allow exponential amplification of the target nucleic acid sequence. Therefore, in preferred embodiments, the second phase amplification reaction is an exponential amplification reaction. Much like the first phase amplification reaction, the second phase amplification reaction is preferably a substantially isothermal reaction, such as, for example, a transcription-associated amplification reaction or a strand displacement amplification reaction. In particularly preferred embodiments, the second phase amplification reaction is a Transcription-Mediated Amplification (TMA) reaction.

The second (or later) phase amplification usually involves contacting the first amplification product with a second phase amplification reaction mixture which, in combination with the first phase amplification reaction mixture, will support exponential amplification of the target nucleic acid sequence. Thus, the second phase amplification reaction mixture typically includes, at a minimum, the one or more component(s) required for exponential amplification that the first phase amplification reaction mixture is lacking. In some embodiments, the second phase amplification reaction mixture includes a component selected from an amplification oligonucleotide, a reverse transcriptase, a polymerase, a nuclease, a phosphorylase, an enzyme co-factor, a chelator, ribonucleotide triphosphates (rNTPs), deoxyribonucleotide triphosphates (dNTPs), $Mg^{2+}$, an optimal pH, an optimal temperature, a salt and a combination thereof. The polymerase is typically selected from an RNA-dependent DNA polymerase, a DNA-dependent DNA polymerase, a DNA-dependent RNA polymerase, and a combination thereof. In some embodiments, the second phase amplification reaction mixture further includes an RNase, such as an RNase H or a reverse transcriptase with an RNase H activity. In some cases, the second phase amplification reaction mixture includes an amplification oligonucleotide, a reverse transcriptase with an RNase H activity, and an RNA polymerase.

The method of the present invention may be used to quantify a target nucleic acid sequence in a biological sample. To this end, the second phase amplification reaction is preferably a quantitative amplification reaction. Typically, the present method will include an additional step of detecting the second amplification product using a variety of detection techniques, e.g., a detection probe, a sequencing reaction, electrophoresis, mass spectroscopy, melt curve analysis, or a combination thereof. Preferably, the second amplification product is quantified using a detection probe. In some embodiments, the quantification step may be performed in real time, which can be accomplished, for example, if the detection probe used for the quantification is a molecular beacon, a molecular torch, a hybridization switch probe, or a combination thereof. The detection probe may be included in the first and/or second phase amplification reactions with substantially equal degree of success.

In some embodiments, the present method further includes a step of contacting the second amplification product with another bolus of an amplification component selected from an amplification oligonucleotide, a reverse transcriptase (e.g., a reverse transcriptase with an RNase H activity), a polymerase (e.g., an RNA polymerase), a nuclease, a phosphorylase, an enzyme co-factor, a chelator, ribonucleotide triphosphates (rNTPs), deoxyribonucleotide triphosphates (dNTPs), $Mg^{2+}$, a salt and a combination thereof. The purpose of this additional step is to provide a boost to the second phase amplification reaction as some of the amplification reaction components may become depleted over time.

A closely related aspect of the present invention is concerned with a method for amplifying a plurality of different target nucleic acid sequences in a sample including the following steps. Initially, the target nucleic acid sequences are subjected to a first phase amplification reaction under conditions that do not support exponential amplification of any of the target nucleic acid sequences. The first phase amplification reaction generates a plurality of first amplification products, which are subsequently subjected to a second (or later) phase amplification reaction under conditions allowing exponential amplification of the first amplification products, thereby generating a plurality of second amplification products.

In a modified version of the second aspect, the invention provides a method for amplifying a plurality of different target nucleic acid sequences in a sample, where some, but not all, of the target nucleic acid sequences are subjected to linear amplification, and/or some, but not all, of the target nucleic acid sequences are subjected to exponential amplification. At least three variants of the first phase amplification are contemplated: (1) some of the target sequences are subjected to linear amplification, and the rest are left unamplified; (2) some of the target sequences are subjected to exponential amplification, and the rest are left unamplified; and (3) some of the target sequences are subjected to linear amplification, and the rest are subjected to exponential amplification. Thus, the first phase amplification may result in amplification of all of the target nucleic acid sequences (option 3) or only a subset thereof (options 1 and 2). The subset of the target nucleic acid sequences may represent targets known to be present in relatively low quantities and/or targets that are difficult to amplify compared to other targets. The first phase amplification reaction generates one or more first amplification product(s). The first amplification product(s) and any unamplified target nucleic acid sequence(s) in the sample are then subjected to a second phase amplification reaction under conditions allowing exponential amplification thereof, generating a plurality of second amplification products.

It is understood that the various optional elements and parameters discussed above in connection with multiphase uniplex (i.e. single target) amplification are also applicable to the multiphase multiplex amplification modes described herein.

C. Compositions for Multiphase Amplification

As noted above, in a third aspect, the present invention provides a composition for amplifying a target nucleic acid sequence in a sample including the following components: (a) an amplification oligonucleotide that hybridizes to a first portion of the target nucleic acid sequence; (b) an optional target capture oligonucleotide that hybridizes to a second portion of the target nucleic acid sequence; and (c) an amplification enzyme. One of the key features of the present composition is that it lacks at least one component required for exponential amplification of the target nucleic acid sequence. As explained in detail elsewhere in this application, one of the advantages of the present composition is that it helps to reduce non-specific amplification, thereby focusing the amplification resources on the target sequence.

In this aspect, the target nucleic acid sequence may be any RNA or DNA sequence. In some embodiments, the portion of the target sequence targeted by the first amplification oligonucleotide may be completely different (e.g. non-overlapping) from the portion targeted by the target capture oligonucleotide (if used). Alternatively, the portion of the target sequence targeted by the first amplification oligonucleotide may fully or partially overlap with, or even be identical to, the portion targeted by the target capture oligonucleotide. In some special cases, the target capture oligonucleotide may also be structurally identical to the amplification oligonucleotide and perform an amplification function in addition to target capture. The target capture oligonucleotide may be directly coupled to a solid support (e.g., via covalent bonding); alternatively, the composition may further include a capture probe coupled to a solid support such that the capture probe hybridizes to a portion of the target capture oligonucleotide. The solid support preferably includes a plurality of magnetic or magnetizable particles or beads that can be manipulated using a magnetic field.

As noted above, the amplification oligonucleotide of the present composition may include a target specific sequence and 5' promoter sequence recognized by an RNA polymerase, such as T7 RNA polymerase. In some embodiments, the composition may include at least two amplification oligonucleotides, one of which may include a 5' promoter sequence for an RNA polymerase (e.g., T7 RNA polymerase). The promoter-containing amplification oligonucleotide may further include a blocked 3' terminus that prevents its enzymatic extension. In those cases where the composition includes two or more amplification oligonucleotides, the oligonucleotides may form a complex, e.g., a DH complex. The DH complex may include a non-promoter amplification oligonucleotide that includes a target specific sequence joined at its 5' terminus to a linking member for linking the non-promoter amplification oligonucleotide to a second amplification oligonucleotide of the DH complex. The second amplification oligonucleotide typically includes a 5' promoter sequence for an RNA polymerase, such as T7 RNA polymerase. As explained in more detail above in connection with single-primer amplification, the second amplification oligonucleotide may sometimes include a blocked 3' terminus that prevents its enzymatic extension. The linking member of the non-promoter amplification oligonucleotide typically includes a nucleotide sequence that is complementary to a portion of the second amplification oligonucleotide. In cases where the second amplification oligonucleotide includes a promoter sequence, the linking member of the first amplification oligonucleotide preferably includes a nucleotide sequence that is complementary to a portion of the promoter sequence of the second amplification oligonucleotide. In some embodiments, at least one of the amplification oligonucleotides may include a tag sequence (e.g., a universal tag) located 5' to a target specific sequence. In addition, the present composition may include a blocker oligonucleotide to prevent enzymatic extension of the target nucleic sequence beyond a desired end-point.

The amplification enzyme of the present composition may be in the form of a reverse transcriptase, a polymerase, or a combination thereof. The polymerase may be selected from an RNA-dependent DNA polymerase, a DNA-dependent DNA polymerase, a DNA-dependent RNA polymerase, and a combination thereof. The composition preferably further includes an RNase, such as an RNase H or a reverse transcriptase with an RNase H activity. In some instances, the composition may further include a detection probe for monitoring the isothermal amplification reaction in real time, which detection probe may be selected from a molecular beacon, a molecular torch, a hybridization switch probe, and a combination thereof.

As noted above, one of the key features of the present composition is its lack of at least one component required for exponential amplification of the target nucleic acid sequence. The lacking component required for exponential amplification may be an amplification oligonucleotide (e.g., a promoter primer or a non-promoter primer), a polymerase (e.g., an RNA polymerase), a nuclease, a phosphorylase, an enzyme co-factor, a chelator, one or more ribonucleotide triphosphates (rNTPs), $Mg^{2+}$, an optimal pH, an optimal temperature, a salt, an optimal salt concentration or a combination thereof. It is understood that this list is not exhaustive and may include other components that are necessary for an exponential amplification reaction to proceed.

Where multiplex amplification is intended, the present composition may include a plurality of different target capture oligonucleotides and a plurality of different amplification oligonucleotides that hybridize to a plurality of different target nucleic acid sequences.

As noted above, the present invention also provides an alternative composition for amplifying a plurality of different target nucleic acid sequences in a sample. This alternative composition includes the following components: (a) a plurality of different amplification oligonucleotide complexes that hybridize to a plurality of different target nucleic acid sequences, where each amplification oligonucleotide complex includes a first amplification oligonucleotide having a first target specific sequence that is directly or indirectly joined to a second amplification oligonucleotide having a second target specific sequence; and (b) an amplification enzyme. Once again, the composition lacks at least one component required for exponential amplification of the target nucleic acid sequences.

One of the first and second amplification oligonucleotides typically includes a 5' promoter sequence for an RNA polymerase, such as T7 RNA polymerase. As explained in more detail above in connection with single-primer amplification, the promoter-containing amplification oligonucleotide may include a blocked 3' terminus that prevents its enzymatic extension. In some embodiments, at least one of the first and second amplification oligonucleotides may also include a tag sequence (e.g., a universal tag) located 5' to a target specific sequence. The composition may further include a blocker oligonucleotide to prevent enzymatic extension of the target nucleic sequence beyond a desired end-point.

In some embodiments, the composition may also include a plurality of different target capture oligonucleotides that hybridize to the target nucleic acid sequences. The target capture oligonucleotide may be directly coupled to a solid support (e.g., via covalent bonding); alternatively, the composition may further include a capture probe coupled to a solid support such that the capture probe hybridizes to a portion of the target capture oligonucleotide. The solid support preferably includes a plurality of magnetic or magnetizable particles or beads that can be manipulated using a magnetic field.

As noted above, methods and compositions disclosed herein are useful for amplifying target nucleic acid sequences in vitro to produce amplified sequences that can be detected to indicate the presence of the target nucleic acid in a sample. The methods and compositions are useful for synthesizing amplified nucleic acids to provide useful information for making diagnoses and/or prognoses of medical conditions, detecting the purity or quality of environmental and/or food samples, or investigating forensic evidence. The methods and compositions are advantageous because they allow synthesis of a variety of nucleic acids to provide highly sensitive assays over a wide dynamic range that are relatively rapid and inexpensive to perform, making them suitable for use in high throughput and/or automated systems. The methods and compositions can be used for assays that analyze single target sequences, i.e., uniplex amplification systems, and are especially useful for assays that simultaneously analyze multiple different target sequences, i.e., multiplex amplification systems. Preferred compositions and reactions mixtures are provided in kits that include defined assay components that are useful because they allow a user to efficiently perform methods that use the components together in an assay to amplify desired targets.

Embodiments of the compositions and methods described herein may be further understood by the examples that follow. Method steps used in the examples have been described herein and the following information describes typical reagents and conditions used in the methods with more particularity. Those skilled in the art of nucleic acid amplification will appreciate that other reagents and conditions may be used that will not substantially affecting the process or results so long as guidance provided in the description above is followed. For example, although Transcription-Mediated Amplification (TMA) methods are described in the examples below, the claimed methods are not limited to TMA-based embodiments. Moreover, those skilled in the art of molecular biology will also understand that the disclosed methods and compositions may be performed manually or in a system that performs one or more steps (e.g., pipetting, mixing, incubation, and the like) in an automated device or used in any type of known device (e.g., test tubes, multi-tube unit devices, multi-well devices such as 96-well microtitre plates, and the like).

EXAMPLES

Exemplary reagents used in the methods described in the examples include the following.

"Sample Transport Medium" or "STM" is a phosphate-buffered solution (pH 6.7) that included EDTA, EGTA, and lithium lauryl sulfate (LLS).

"Target Capture Reagent" or "TCR" is a HEPES-buffered solution (pH 6.4) that included lithium chloride and EDTA, together with 250 µg/ml of magnetic particles (1 micron SERA-MAG™ MG-CM particles, Seradyn, Inc. Indianapolis, Ind.) with $(dT)_{14}$ oligonucleotides covalently bound thereto.

"Target Capture Wash Solution" or "TC Wash Solution" is a HEPES-buffered solution (pH 7.5) that included sodium chloride, EDTA, 0.3% (v/v) absolute ethanol, 0.02% (w/v) methyl paraben, 0.01% (w/v) propyl paraben, and 0.1% (w/v) sodium lauryl sulfate.

"Amplification Reagent" or "AR" is a HEPES-buffered solution (pH 7.7) that included magnesium chloride, potassium chloride, four deoxyribonucleotide triphosphates (dATP, dCTP, dGTP, and dTTP), four ribonucleotide triphosphates (rATP, rCTP, rGTP, and rUTP). Primers and/or probes may be added to the reaction mixture in the amplification reagent, or may be added separate from the reagent (primerless amplification reagent).

"Enzyme Reagents" or "ER", as used in amplification or pre-amplification reaction mixtures, are HEPES-buffered solutions (pH 7.0) that include MMLV reverse transcriptase (RT), T7 RNA polymerase, salts and cofactors.

Example 1

Standard Single-Phase Amplification Protocol

An exemplary protocol for standard single-phase TMA reactions that detect results in real time follows. The assay includes purification of target nucleic acids before amplification, amplification, and detection of the amplified products during amplification.

Target capture is performed substantially as previously described in detail (U.S. Pat. Nos. 6,110,678, 6,280,952 and 6,534,273). Briefly, samples are prepared to contain known amounts of target RNA (in vitro transcripts ("IVT") present at a predetermined copy level per sample in a total volume of 400 ml of a 1:1 (v:v) mixture of water and sample transport medium). Each sample is mixed with 100 ml of TCR that typically contains 5 pmol of target capture oligonucleotide (TCO) specific for the analyte nucleic acid to be captured (i.e., 3' target-specific binding region) and a 5' tail region (e.g., $dT_3A_{30}$ sequence) for binding to the immobilized probe (e.g., poly-T oligonucleotides attached to paramagnetic particles; 12.5 µg of particles with attached oligonucleotides per reaction). The mixtures are incubated for 25 to 30 min at 60±1° C. and then for 25 to 30 min at room temperature (20 to 25° C.) to form hybridization complexes through which target nucleic acids are bound to the paramagnetic particles isolated via magnetic separation (e.g., KingFisher96™ magnetic particle processor, Thermo Fisher Scientific, Inc., Waltham, Mass.) and washed one time using TC wash solution.

Particles are re-suspended in 0.075 ml of amplification reagent and with amplification oligonucleotides used in the amplification. Detection probes (e.g., molecular beacon or molecular torch probes labeled with a fluorescent label compound) may be added with amplification oligonucleotides, or with addition of enzymes, or following addition of enzymes. Reaction mixtures are covered to prevent evaporation and incubated for 1 to 2 minutes at 42±0.5° C. While keeping them at 42±0.5° C., the mixtures were uncovered and mixed with 0.025 ml of enzyme reagent per mixture, covered again, and incubated for 30 to 40 minutes at 42±0.5° C., during which time fluorescence was measured at regular time intervals (e.g., every minute or several reads per minute) which are referred to as "cycles" for data collection and display, which is typically a graph of detected fluorescence units versus time, from which a time of emergence of signal is determined ("TTime," i.e. the time at which fluorescence signal for a sample becomes positive over a predetermined background level).

Example 2

Evaluation of Dual-Phase HIV-1 Amplification in Forward TMA Format

In this example, dual-phase forward TMA was evaluated using a human immunodeficiency virus 1 (HIV-1), subtype B target template containing the pol region.

In the dual-phase amplification approach used here, which is briefly summarized in FIG. 1, a T7 primer was hybridized to the target HIV-1 sequence during target capture, followed by removal of excess T7 primer. The amplification process was divided into two distinct phases. During the first phase, a non-T7 primer was introduced along with all of the requisite amplification, detection and enzyme reagents, with the exception of additional T7 primer. In the presence of reverse transcriptase, the T7 primer hybridized to the target was extended, creating a cDNA copy, and the target RNA template was degraded by the reverse transcriptase's RNase H activity. The non-T7 primer subsequently hybridized to the cDNA and was then extended, filling in the promoter region of the T7 primer and creating an active, double-stranded template. T7 polymerase then produced multiple RNA transcripts from the template. The non-T7 primer subsequently hybridized to the RNA transcripts and was extended, producing promoterless cDNA copies of the target RNA template. The RNA strands were degraded by RNase activity of the reverse transcriptase. Because no T7 primer was available in the phase 1 amplification mixture, the reaction could not proceed any further. The second phase was then started with the addition of T7 primer, thus initiating exponential amplification of the cDNA pool produced in phase 1.

Figure 2A:
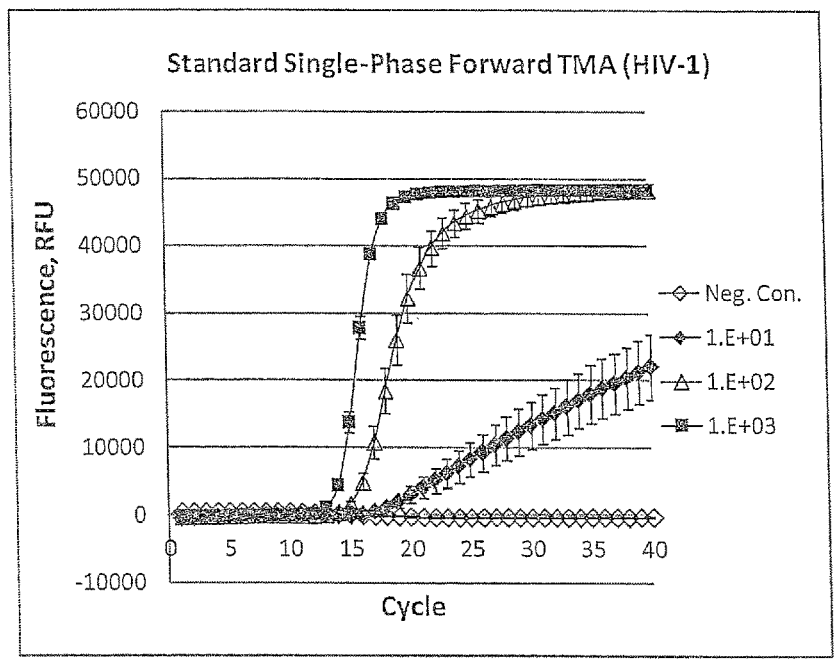
FIGS. 2A-2B show a comparison between the standard single-phase forward TMA (FIG. 2A) and a modified single-phase forward TMA that was used as a control in some of the working examples described herein (FIG. 2B). The standard single-phase forward TMA protocol is well-known in the art and is described in detail elsewhere in the present application. In the modified single-phase TMA protocol, a T7 primer hybridizes to a target nucleic acid sequence during target capture, thereby eliminating the usual T7 primer annealing step at 60° C. following the target capture. Subsequently, a non-T7 primer is added along with additional T7 primer and all of the requisite amplification and enzyme reagents, thus allowing exponential amplification to proceed. As one can see from FIGS. 2A and 2B, both of the single-phase TMA protocols appear to have comparable sensitivities at the low end, reliably detecting 100 or more copies of a human immunodeficiency virus 1 (HIV-1) target template but performing poorly at 10 copies of the target template.
Figure 2B:
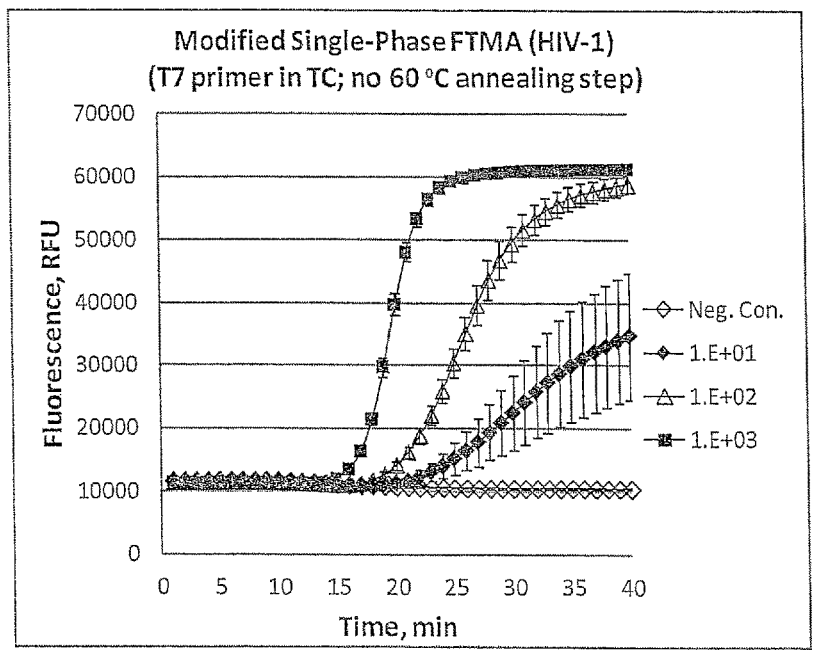
Figure 3A:
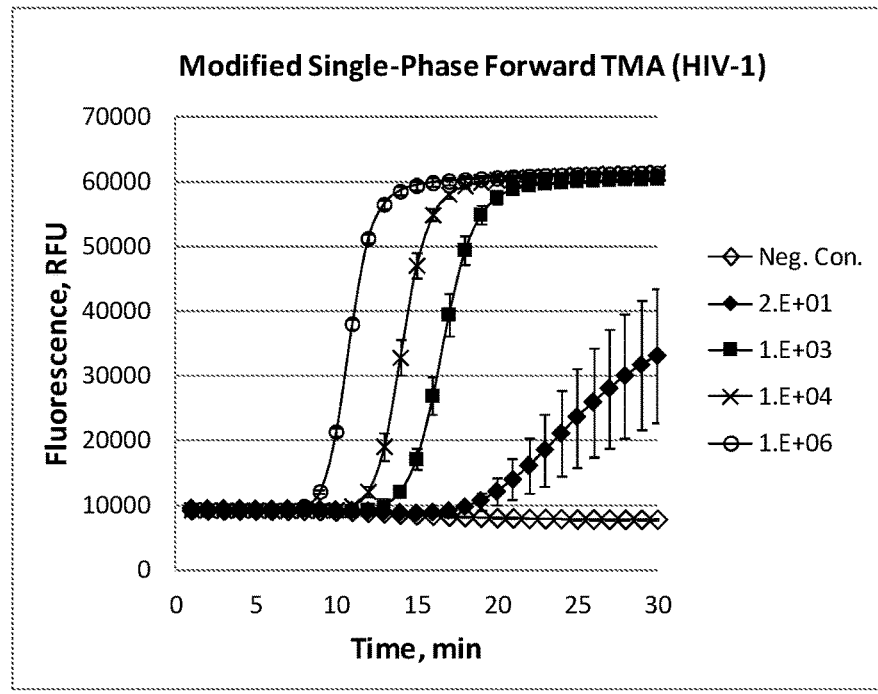
FIGS. 3A-3C demonstrate a comparison between the modified single-phase forward TMA and dual-phase forward TMA.
Figure 3B:
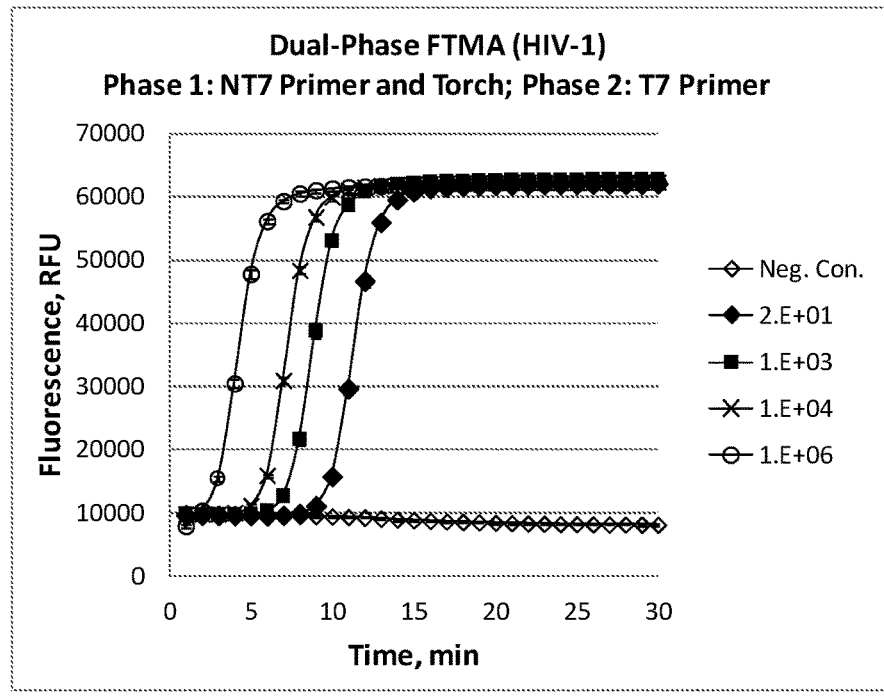
Figure 3C:
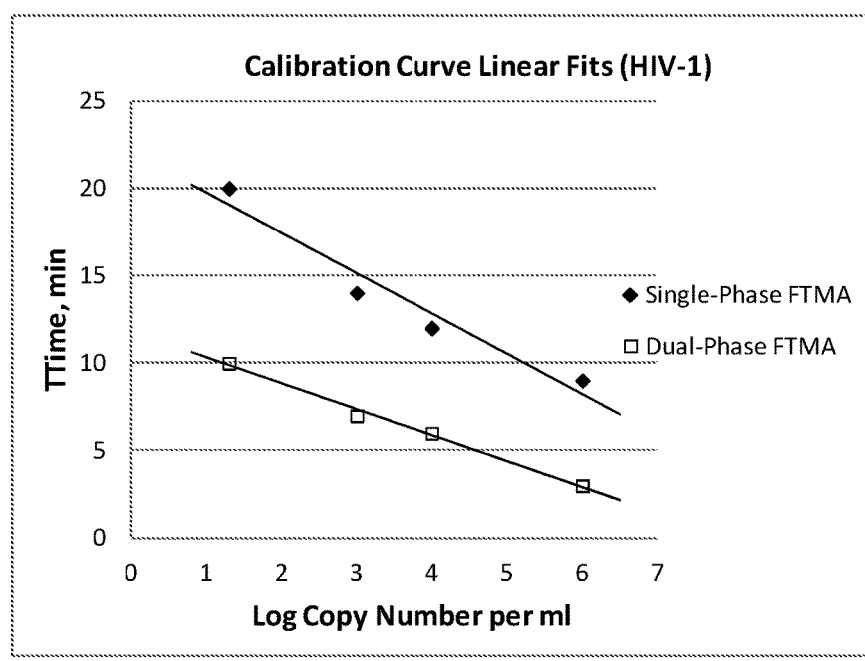
Figure 4A:
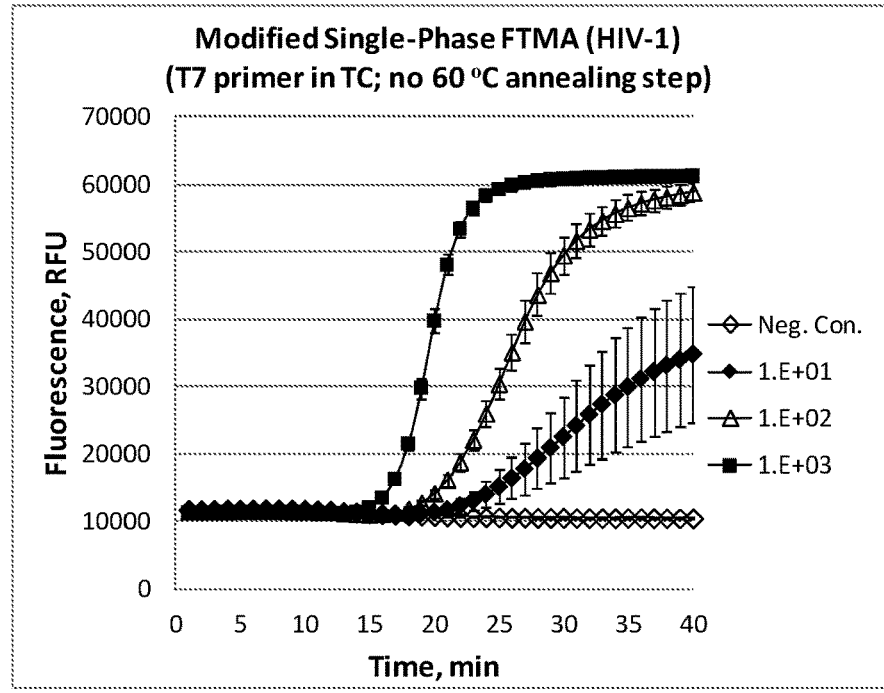
FIGS. 4A-4D illustrate optimization of the concentration of T7 primer added in the second phase of amplification.
Figure 4B:
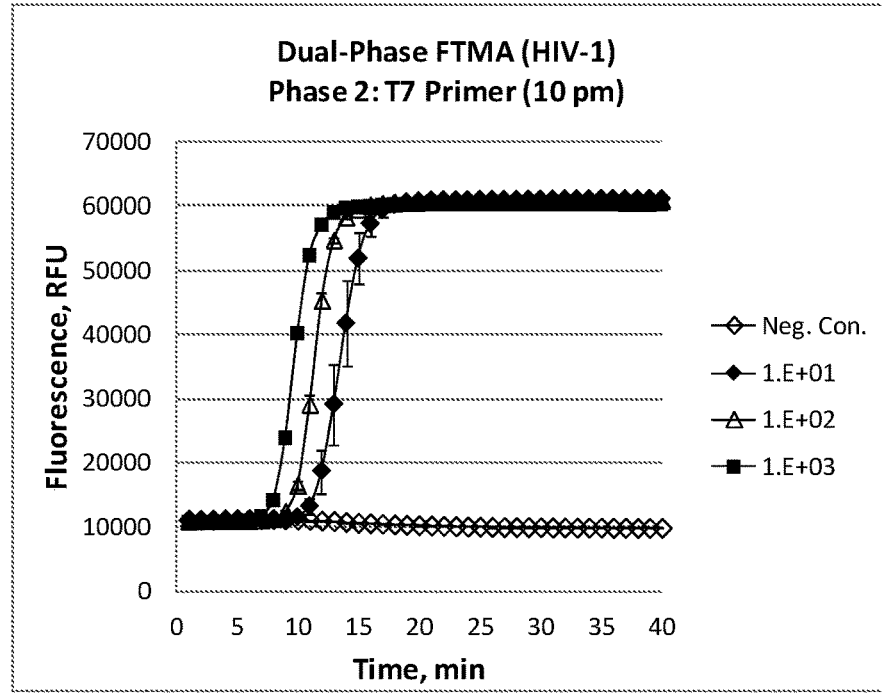
Figure 4C:
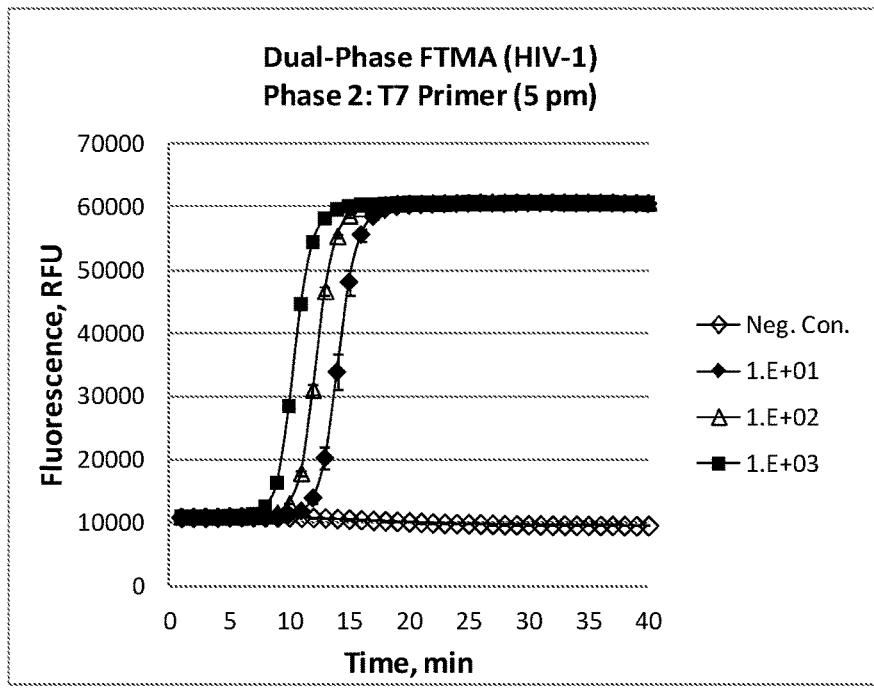
Figure 4D:
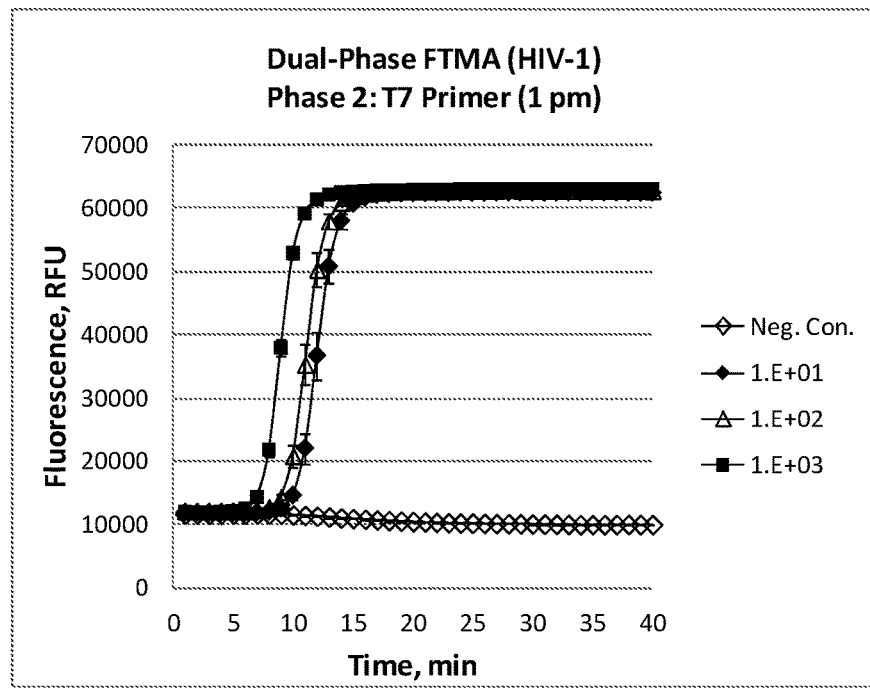

Results from the initial evaluation of the dual-phase approach are shown in FIGS. 3A-3C. FIG. 3A shows results of a single-phase amplification experiment that was modified to mimic the dual-phase format. More specifically, the T7 primer was added during the target capture step (allowing the standard 60° C. annealing step to be eliminated from the protocol); no primers or Enzyme Reagent were added in the first phase; and non-T7 and T7 primers as well as Enzyme Reagent were added to the second phase for the initiation of exponential amplification. To address the concern that this modified protocol for the standard single-phase control may have somewhat compromised its performance, we compared the modified single-phase forward protocol to the standard single-phase forward TMA (FIGS. 2A-2B). As one can see from FIGS. 2A and 2B, the two protocols resulted in highly similar levels of precision and sensitivity of detection. In contrast, the dual-phase protocol yielded significantly improved sensitivity and precision at the low end of analyte concentration (~20 copies/rxn) compared with the standard single-phase format under these conditions (FIG. 3B). Notably, the dual-phase format yielded superior performance both in terms of precision and shorter detection time (FIG. 3C).

Example 3

Optimization of Dual-Phase HIV-1 Amplification Parameters

The first priority in the optimization process was to slow the emergence times and separate the individual target input levels to allow accurate and precise quantification, as well as reduce any putative interference with the non-T7 primer. This was accomplished by titrating down the T7 primer concentration in the second phase (amount used in the dual-phase reaction depicted in FIG. 3B was 10 pmol/rxn). The assay was shown to retain 10 copies/rxn sensitivity and high precision with the lowest amount of T7 provider tested (1.0 pmol/rxn; FIGS. 4A-4D).

Figure 5A:
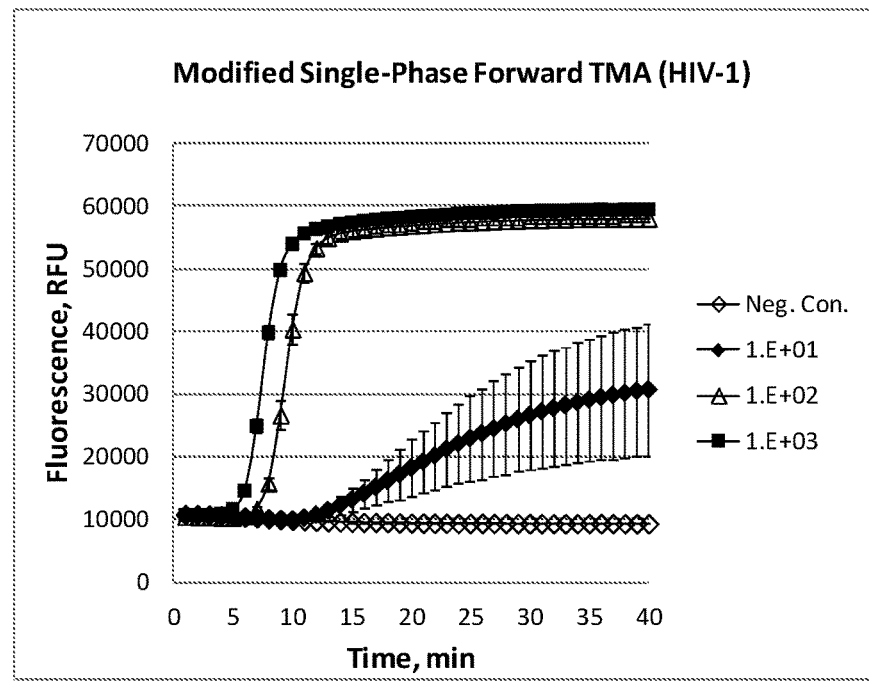
FIGS. 5A-5D show optimization of the concentration of non-T7 primer added in the first phase of amplification.
Figure 5B:
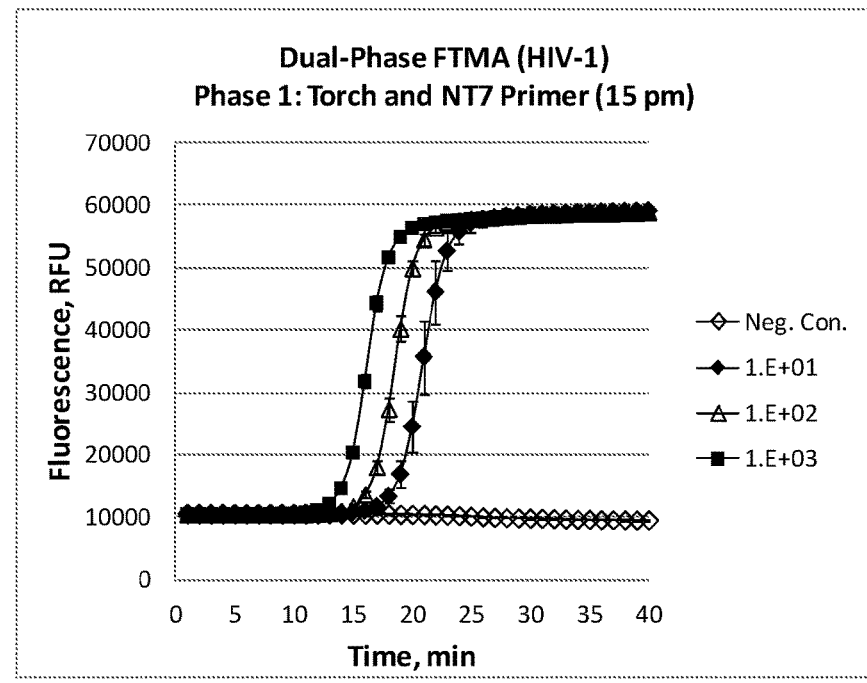
Figure 5C:
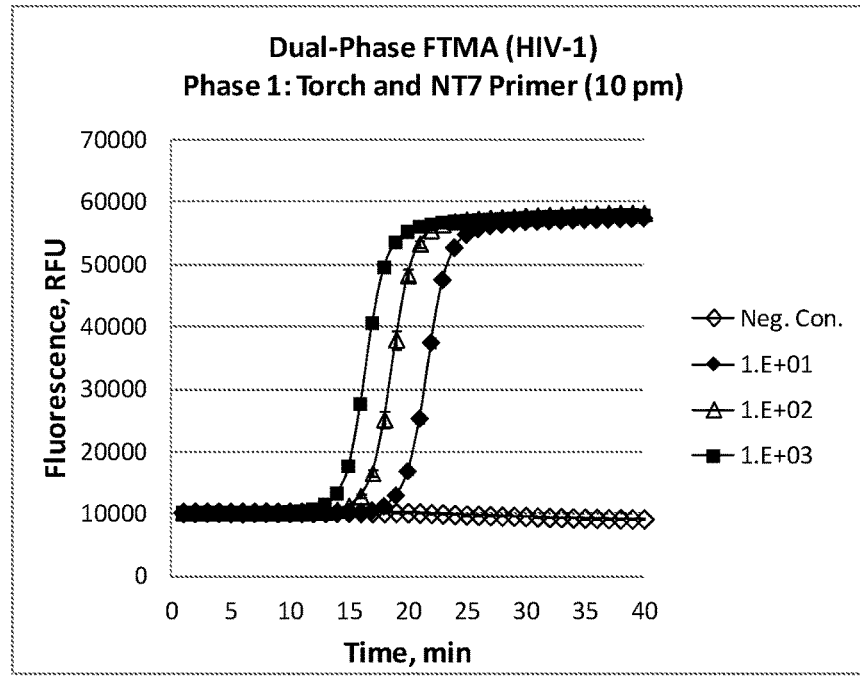
Figure 5D:
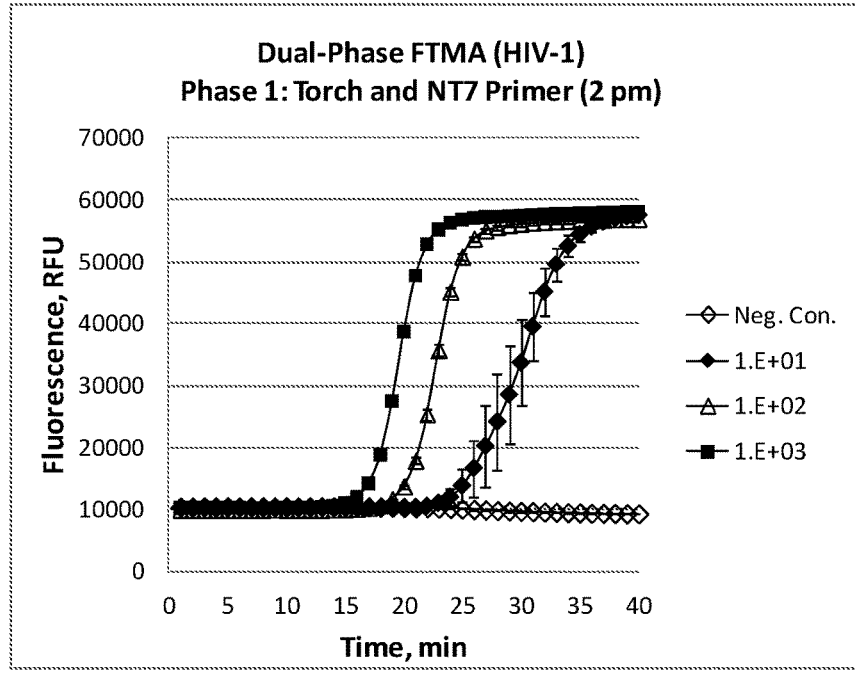

Likewise, the non-T7 primer was also titrated down (amount used in the dual-phase reaction depicted in FIG. 3B was 15 pmol/rxn) while keeping the T7 primer constant at 1 pmol/rxn. A level of 10 pmol/rxn was found to be sufficient for sensitive amplification without losing precision (FIG. 5A). At a level of 2 pmol/rxn of non-T7 primer, the precision at 10 copies/rxn was not as good as with 10 pmol/rxn of non-T7 primer (FIG. 3B), but the performance of the assay was still superior to that of the single-phase control (FIG. 3A).

Thus, the present inventors unexpectedly found that the dual-phase amplification format allows substantially reducing primer concentrations and still attaining superior performance compared to the single-phase format, while reducing side product formation and multiplex interference.

Figure 6A:
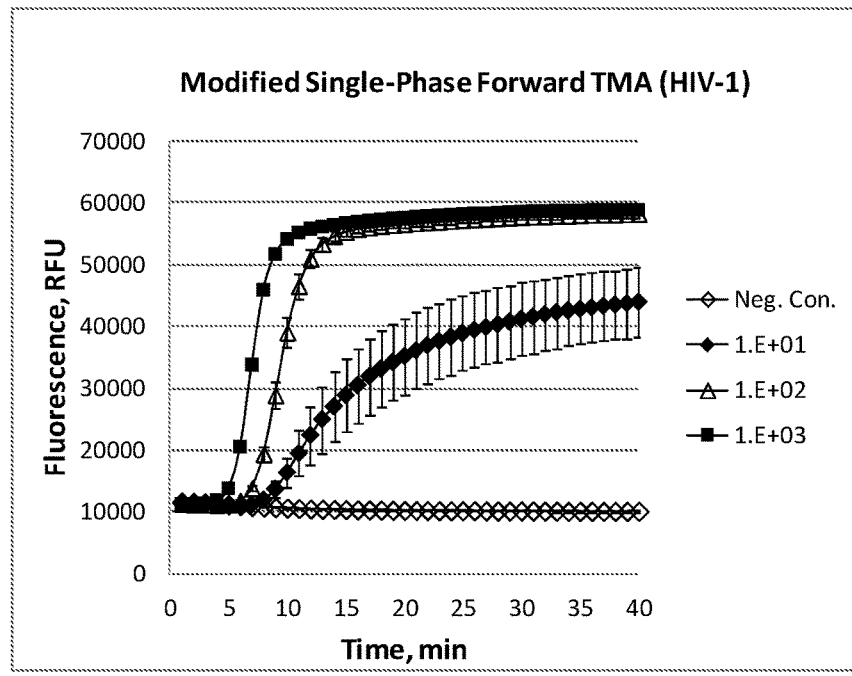
FIGS. 6A-6C demonstrate the effect of the enzyme reagent (RT and T7 RNA polymerase) in the second phase amplification on the overall assay performance.
Figure 6B:
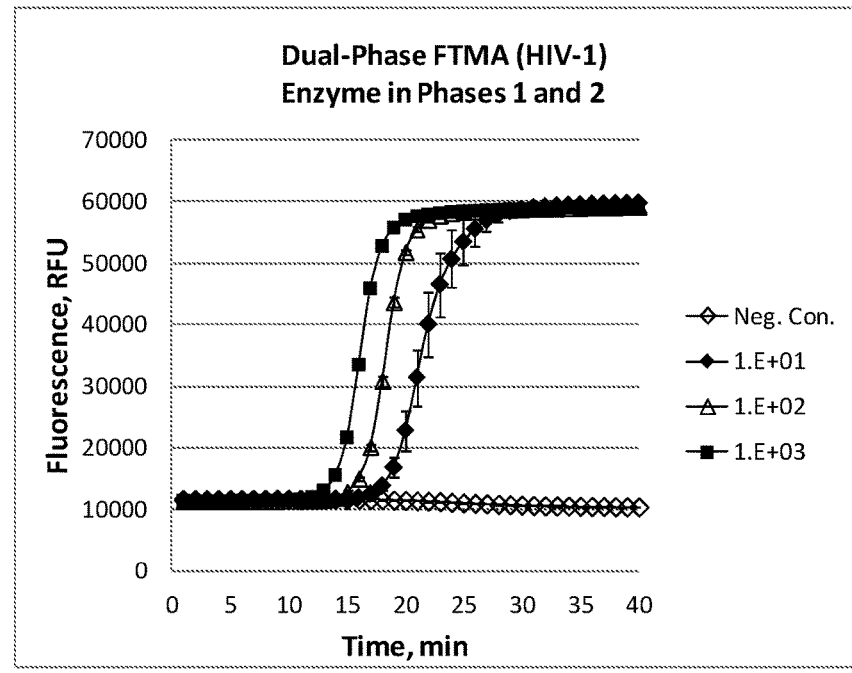
Figure 6C:
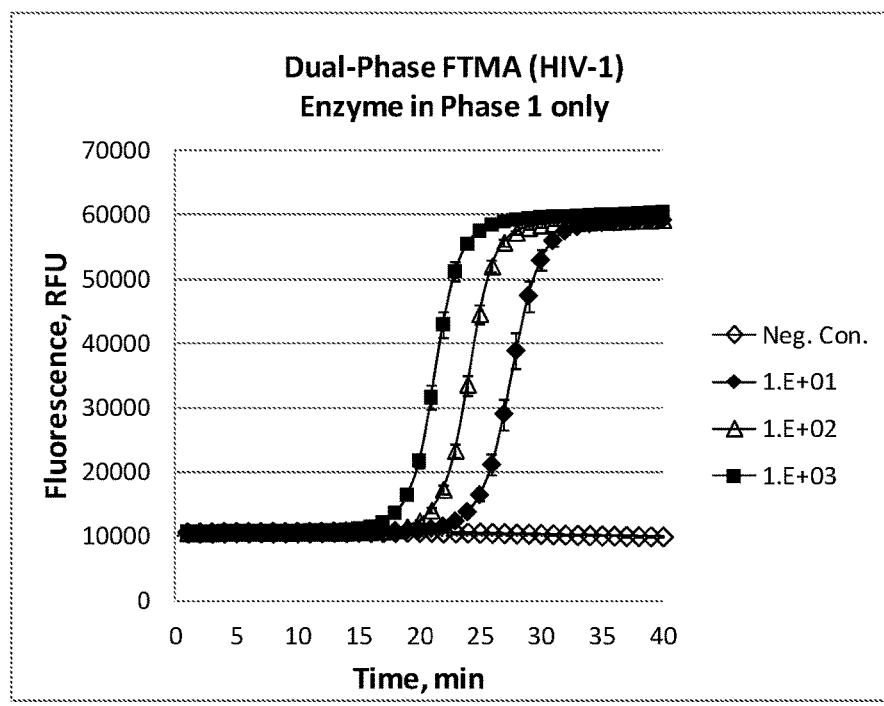

The need for an additional bolus of enzyme in the second phase was also examined (FIGS. 6A-6C). Restriction of enzyme addition to the first phase resulted in a moderate improvement in precision at the low end of analyte concentrations tested (FIGS. 6B and 6C). Further, each copy level emerged approximately five minutes later relative to the dual-phase format where the enzyme reagent was present in both phases. However, the previously observed improvement in sensitivity was retained.

Example 4

Dual-Phase Amplification of HPV16

To determine whether the dual-phase amplification format has broad applicability beyond HIV-1 detection, it was tested on the human papillomavirus subtype 16 (HPV16).

The dual-phase amplification protocol was essentially the same as the one described above in Example 2. Briefly, a T7 primer was hybridized to the target HPV16 sequence during target capture, followed by removal of excess T7 primer. In the first phase of amplification, a non-T7 primer was added along with all of the requisite amplification, detection and enzyme reagents, with the exception of additional T7 primer. After five minutes at 42° C., the T7 primer was added to the reaction mixture to initiate the exponential amplification phase, which was also carried out at 42° C. with real-time detection. The single-phase control experiment was carried out using the same primers and detection probe in the standard single-phase forward TMA format as described in Example 1.

Figure 7A:
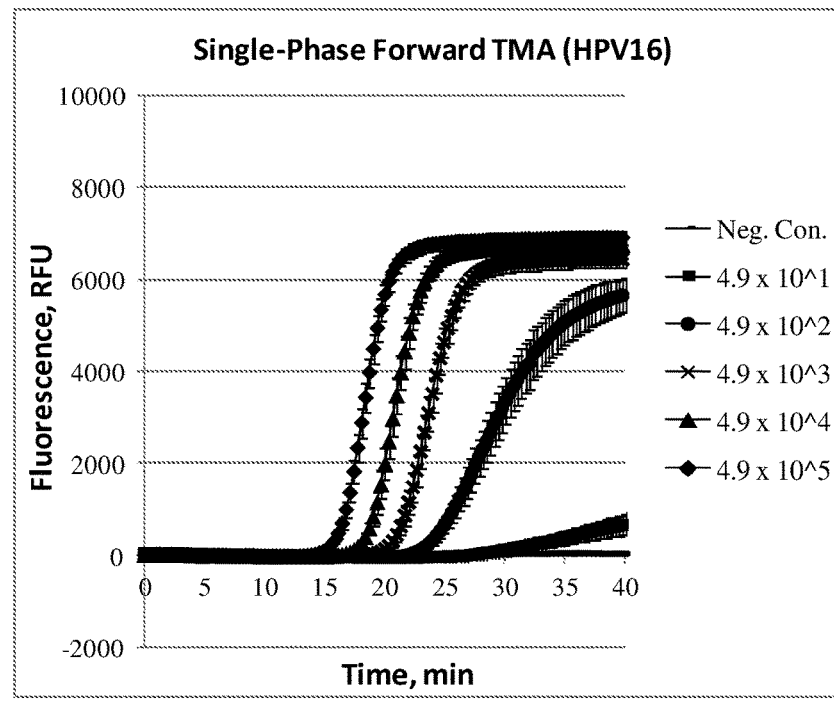
FIGS. 7A-7C show a comparison between the standard single-phase (FIG. 7A) and dual-phase (FIG. 7B) forward TMA using a human papillomavirus subtype 16 (HPV16) target template. As discussed above in reference to HIV-1 target template, in the dual-phase format, the T7 primer was withheld from the amplification mixture in phase 1 and was provided in the second phase to initiate exponential amplification.
Figure 7B:
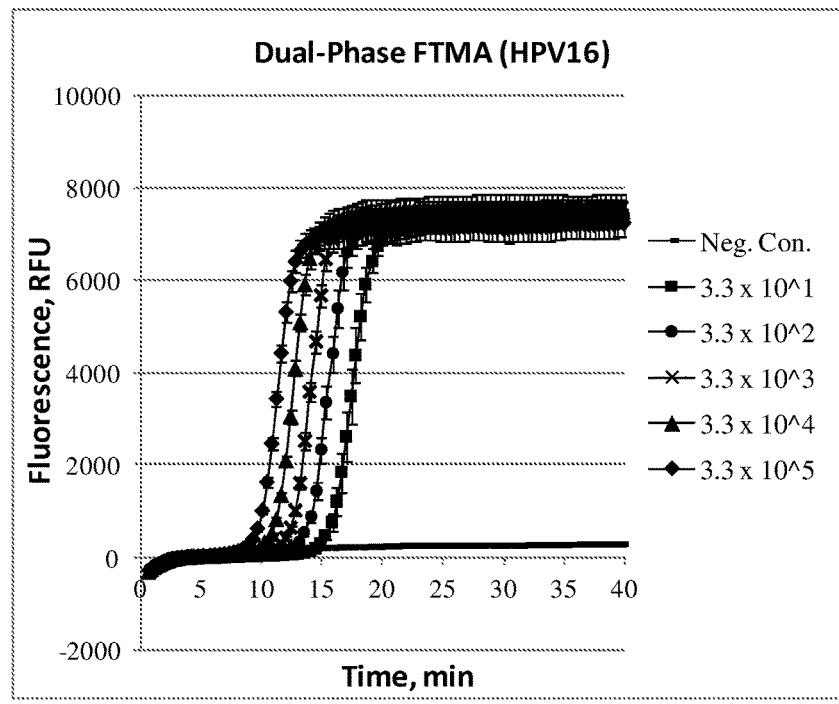
Figure 7C:
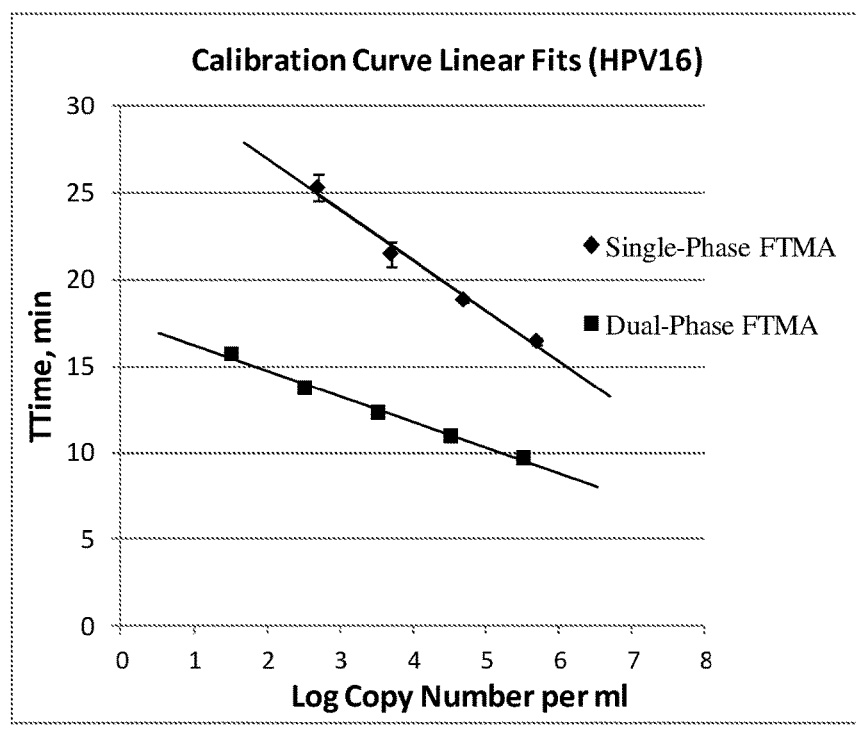

Results of the HPV16 amplification experiment are shown in FIGS. 7A-7C. As shown in FIG. 7A, the single-phase format was able to detect the target template down to ~500 copies/mL (~200 copies/rxn), whereas the dual-phase format improved the sensitivity over 15 fold to ~30 copies/mL (~13 copies/rxn) (FIG. 7B). Further, consistent with our prior observations, the dual-phase amplification format was associated with a significant reduction in the time of detection compared with the single-phase format (FIG. 7C).

Example 5

Dual-Phase Amplification of PCA3

In addition, the dual-phase amplification format was tested on the prostate cancer antigen 3 (PCA3).

A similar dual-phase amplification protocol was used. Briefly, a T7 primer was hybridized to the target PCA3 sequence during target capture, followed by removal of excess T7 primer. In the first phase of amplification, a non-T7 primer was added along with all of the requisite amplification and enzyme reagents, with the exception of additional T7 primer and a molecular torch detection probe. After five minutes at 42° C., the T7 primer and the detection probe were added to the reaction mixture to start the exponential amplification phase, which was also carried out at 42° C. with real-time detection. The single-phase control experiment was carried out using the same primers and detection probe in the standard single-phase TMA format.

Figure 8A:
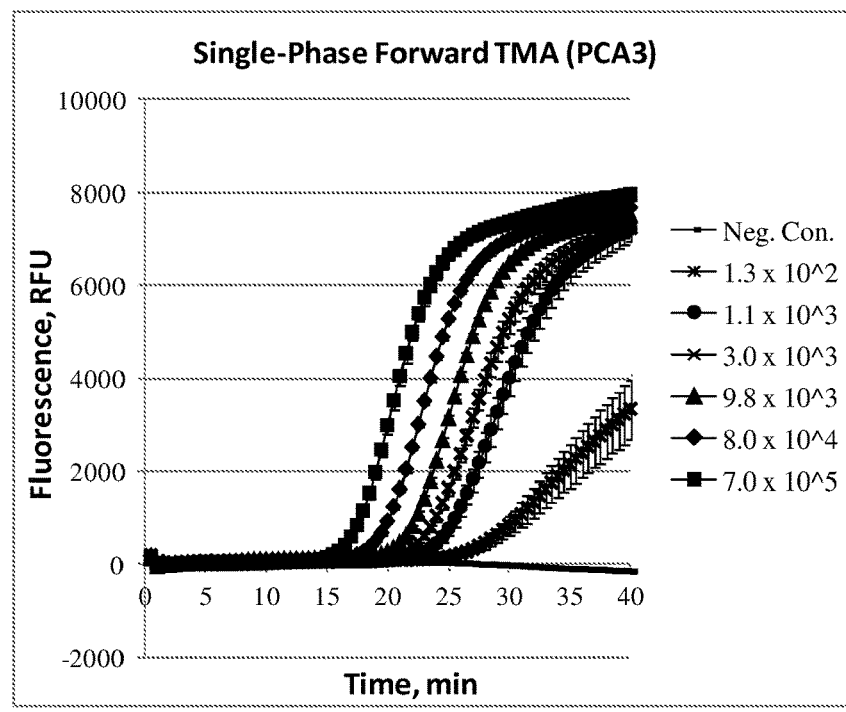
FIGS. 8A-8C show a comparison between the standard single-phase (FIG. 8A) and dual-phase (FIG. 8B) forward TMA using a prostate cancer antigen 3 (PCA3) target template. As discussed above in reference to HIV-1 and HPV16 target templates, in the dual-phase format, the T7 primer was withheld from the amplification mixture in phase 1 and was provided in the second phase to initiate exponential amplification.
Figure 8B:
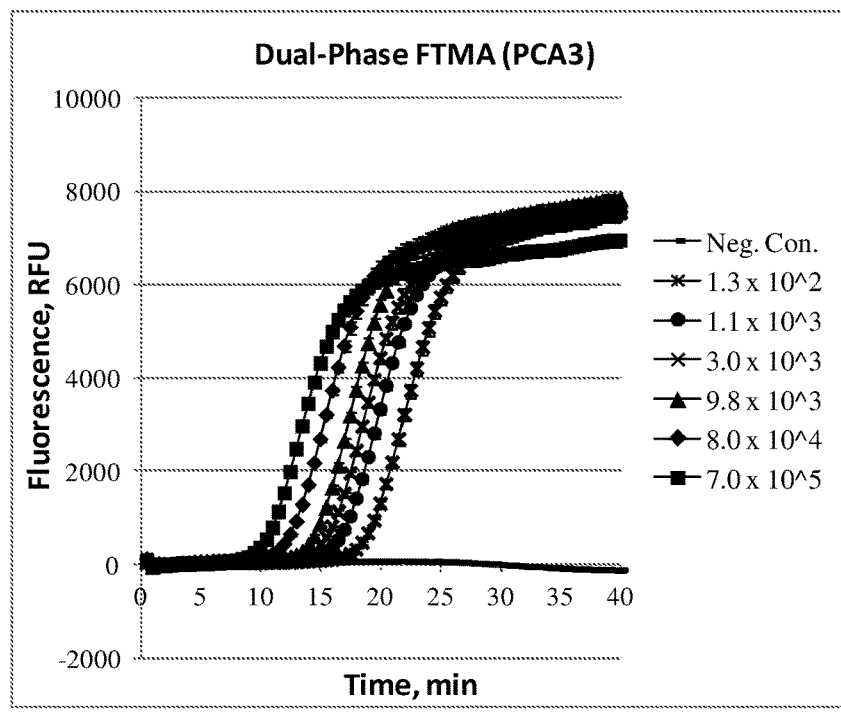
Figure 8C:
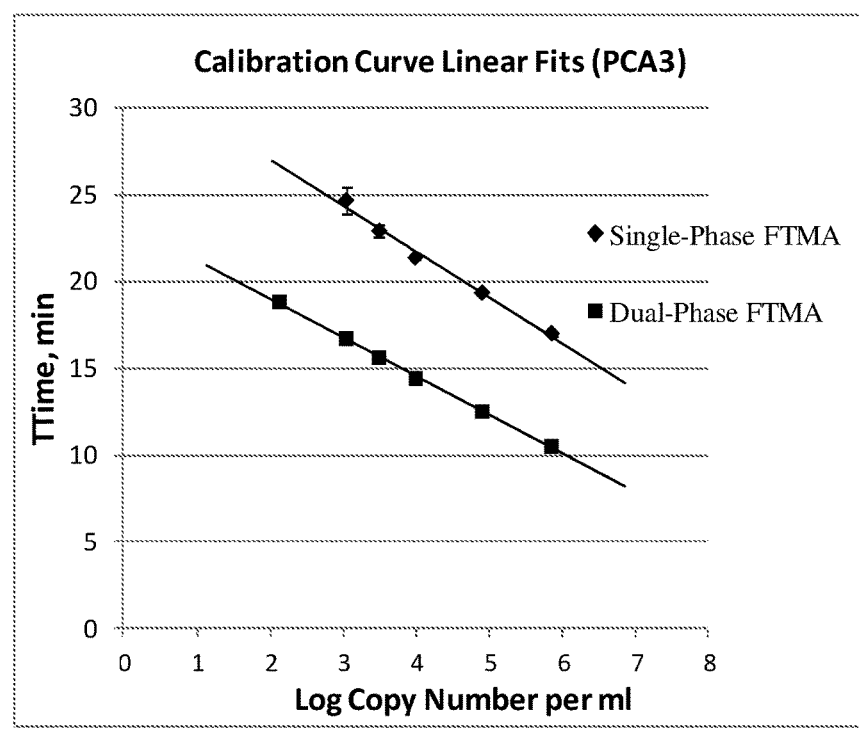

Results of the PCA3 amplification experiment are shown in FIGS. 8A-8C. As one can see from FIGS. 8A-8B, the dual-phase format yielded a significantly improved sensitivity and precision at the low end of analyte concentration (~130 copies/ml, which equivalent to ~50 copies/rxn) compared with the standard single-phase format. In addition, similar to our prior observations, the dual-phase amplification format was associated with a significant reduction in the time of detection compared with the single-phase format (FIG. 8C).

Example 6

Dual-Phase Co-Amplification of PCA3 and T2-ERG

Next, we employed the dual-phase amplification format for simultaneous amplification of multiple targets. In this example, PCA3 and T2-ERG target templates were co-amplified using the dual-phase forward TMA protocol to determine whether duplex amplification will result in the same improvement in sensitivity and precision we have observed previously in uniplex assays (Examples 2-5), as well as provide a reduction in the interference between analytes which is often observed in a standard single phase format.

Briefly, T7 primers were hybridized to the target PCA3 and T2-ERG sequences during target capture, followed by removal of excess T7 primers. In the first phase of amplification, non-T7 primers were added along with all of the requisite amplification, detection and enzyme reagents, with the exception of additional T7 primers. After five minutes at 42° C., the T7 primers were added to the reaction mixture to initiate the exponential amplification phase, which was also carried out at 42° C. with real-time detection in two different fluorescent channels (one for each target). The single-phase control experiment was carried out using the same primers and detection probes in the standard single-phase forward TMA format as described in Example 1.

Figure 9A:
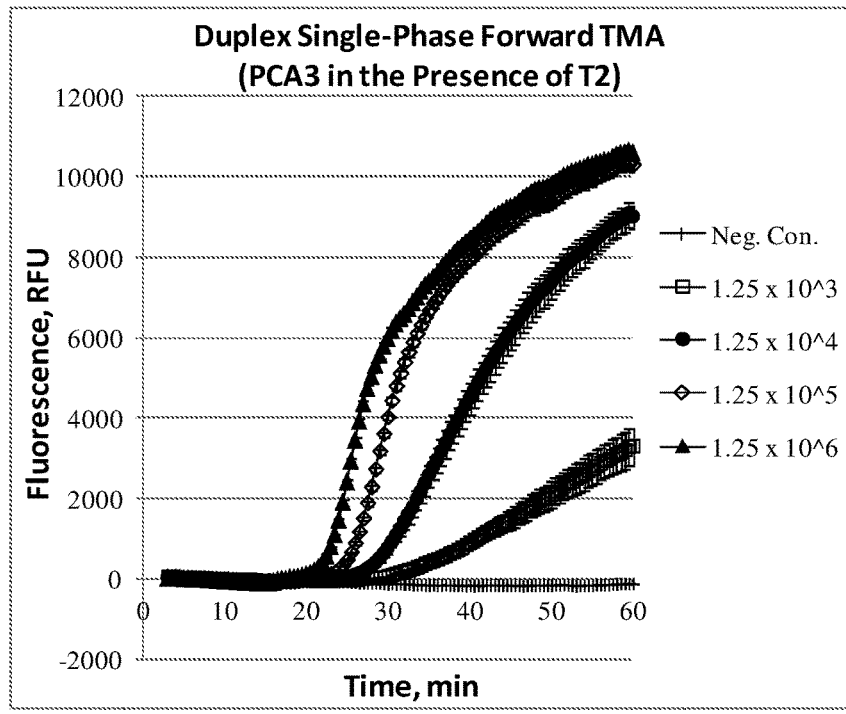
FIGS. 9A-9F show a comparison between the standard single-phase (FIGS. 9A and 9D) and dual-phase (FIGS. 9B and 9E) forward TMA used for duplex amplification of PCA3 and T2-ERG, a prostate cancer marker formed by gene fusion of the androgen-regulated transmembrane serine protease (TMPRSS2) with the ETS transcription factor (ERG).
Figure 9B:
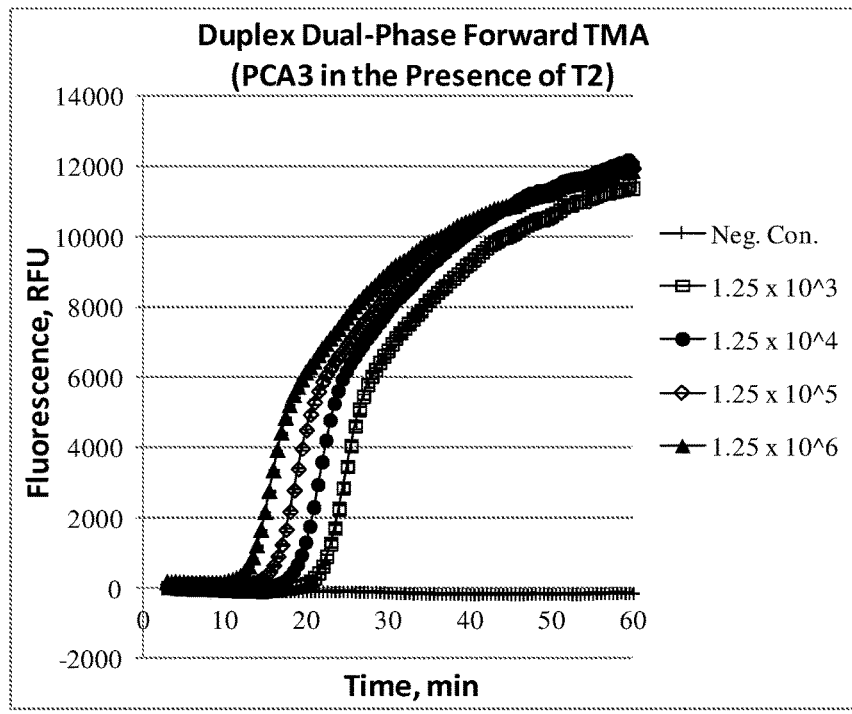
Figure 9C:
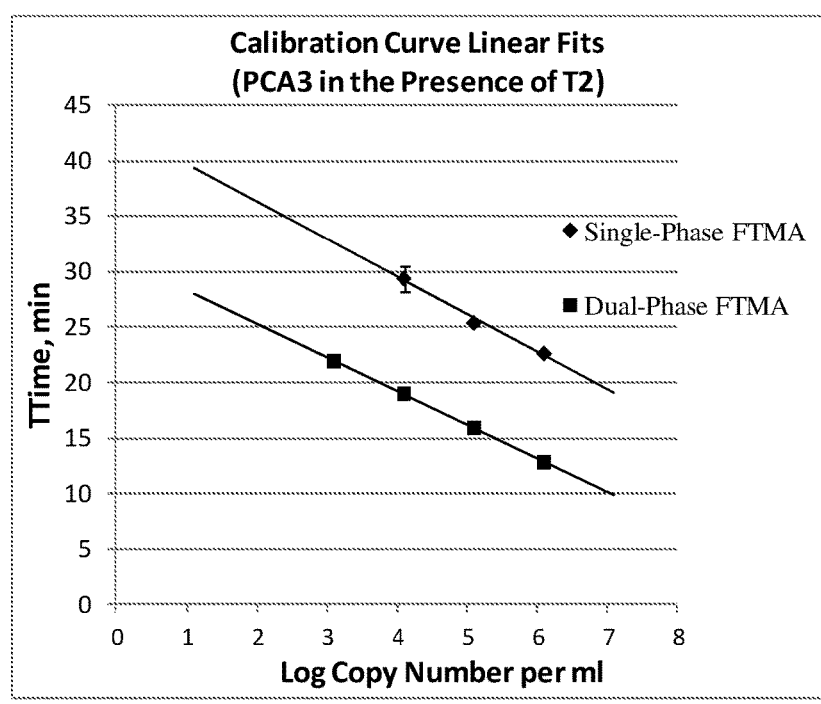

Results of the PCA3 amplification in the presence of T2-ERG are shown in FIGS. 9A-9C. As one can see from FIGS. 9A-9B, the dual-phase format yielded a significantly improved sensitivity and precision at the low end of analyte concentration (~1,250 copies/ml, which is equivalent to ~500 copies/rxn) compared with the standard single-phase format. These results demonstrate that the dual-phase format is effective in reducing analyte-analyte interference in a multiplex reaction. Further, consistent with our prior observations, the dual-phase amplification format was associated with a significant reduction in the time of detection compared with the single-phase format (FIG. 9C).

Figure 9D:
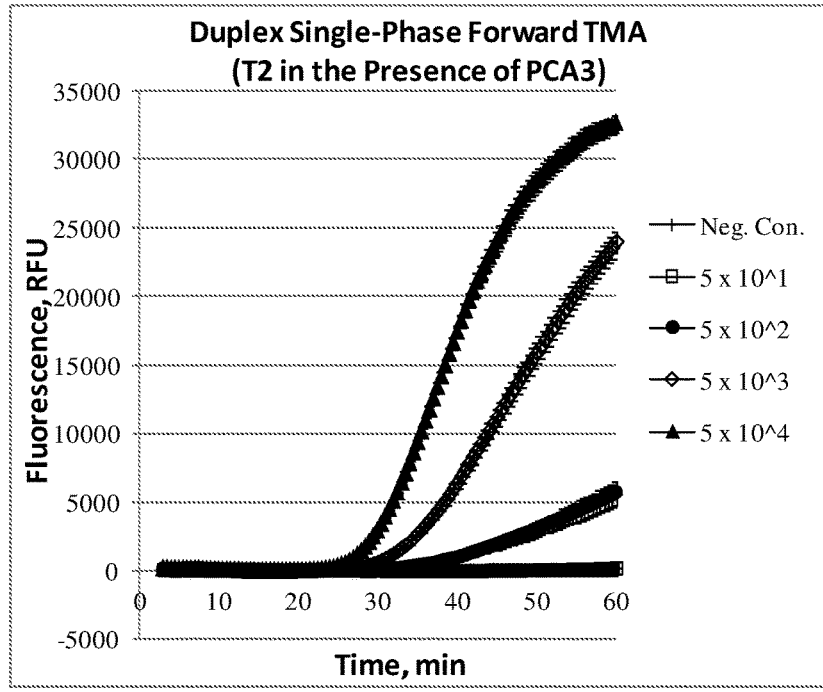
Figure 9E:
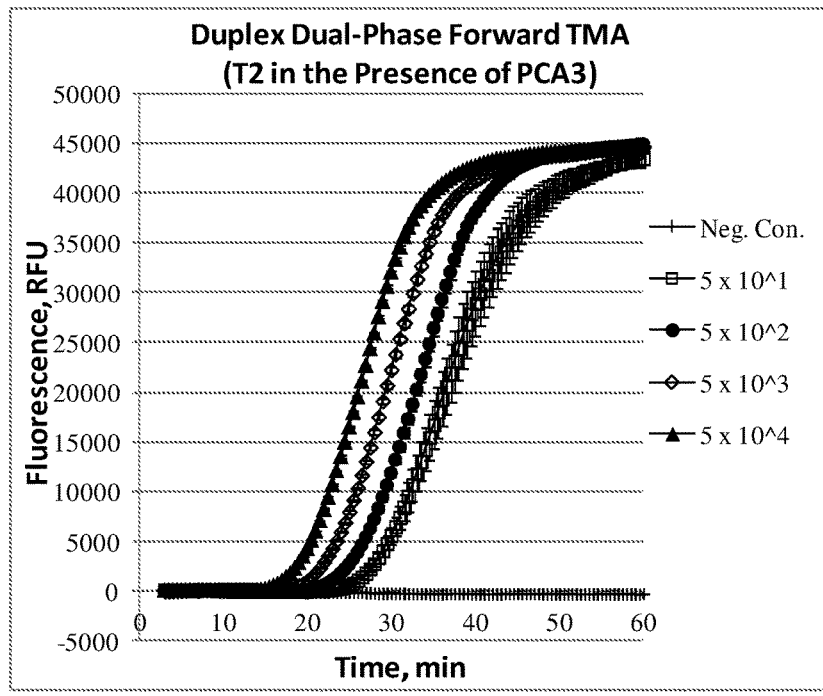
Figure 9F:
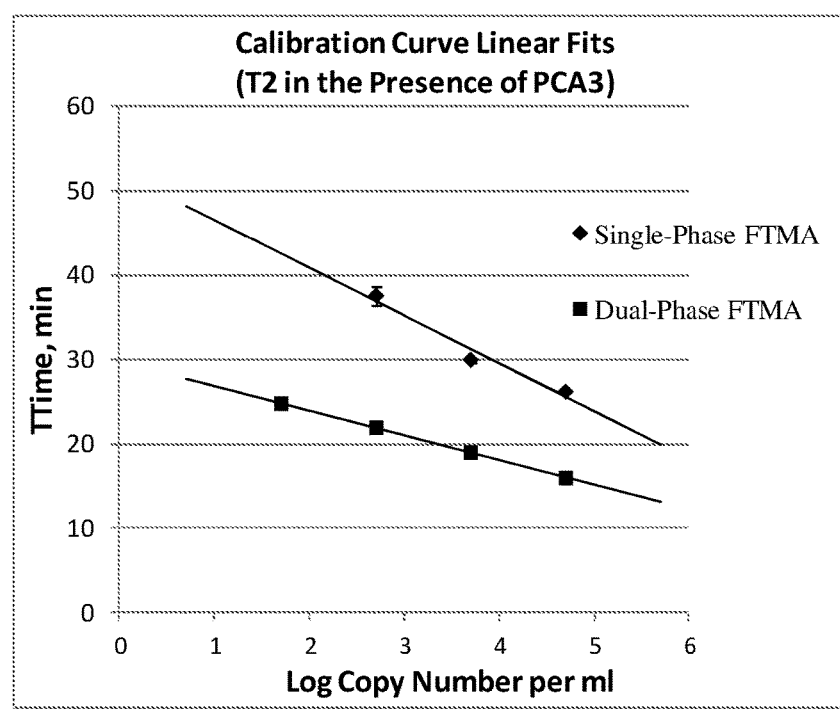

Results of the T2-ERG amplification in the presence of PCA3 are shown in FIGS. 9D-9F. As shown in FIG. 9D, the single-phase format was able to detect the target template down to ~500 copies/mL (~200 copies/rxn), whereas the dual-phase format improved the sensitivity at least 10 fold to ~50 copies/mL (~20 copies/rxn) (FIG. 9E). These results also demonstrate that the dual-phase format is effective in reducing analyte-analyte interference in a multiplex reaction. Further, consistent with our prior observations, the dual-phase amplification format was associated with a significant reduction in the time of detection compared with the single-phase format (FIG. 9F).

Notably, the combined advantages of improved assay sensitivity and precision, and reduced interference among competing reactions in the multiplex amplification format (i.e., as evidenced by comparison of single analyte and dual analyte performance, such as the performance of PCA3 alone in a single phase format as shown in FIG. 8A, where $1.1 \times 10^3$ copies yields a strong signal, and the performance of PCA3 in the presence of T2 in a single phase format as shown in FIG. 9A, where $1.25 \times 10^3$ copies of PCA3 yields a weak signal (due to interference from T2), and performance of PCA3 in the presence of T2 in a dual phase format as shown in FIG. 9B, where $1.25 \times 10^3$ copies of PCA3 yields a very strong signal as the result of a significant reduction in the interference due to T2) was a general feature of the dual-phase formatted assays. These dramatic advantages would not have been predicted in advance of this showing. Additional demonstrations of this feature of the dual-phase nucleic acid amplification method follow.

Example 7

Dual-Phase Co-Amplification of PCA3, PSA and T2-ERG

In this example, PCA3, PSA and T2-ERG target templates were co-amplified using the dual-phase forward TMA protocol to determine whether triplex amplification will result in the same improvement in sensitivity and precision we have observed previously in uniplex and duplex assays (Examples 2-6).

Briefly, T7 primers were hybridized to the target PCA3, PSA and T2-ERG sequences during target capture, followed by removal of excess T7 primers. In the first phase of amplification, non-T7 primers were added along with all of the requisite amplification, detection and enzyme reagents, with the exception of additional T7 primers. After five minutes at 42° C., the T7 primers were added to the reaction mixture to initiate the exponential amplification phase, which was also carried out at 42° C. with real-time detection in three different fluorescent channels (one for each target). The single-phase control experiment was carried out using the same primers and detection probes in the standard single-phase forward TMA format as described in Example 1.

Figure 10A:
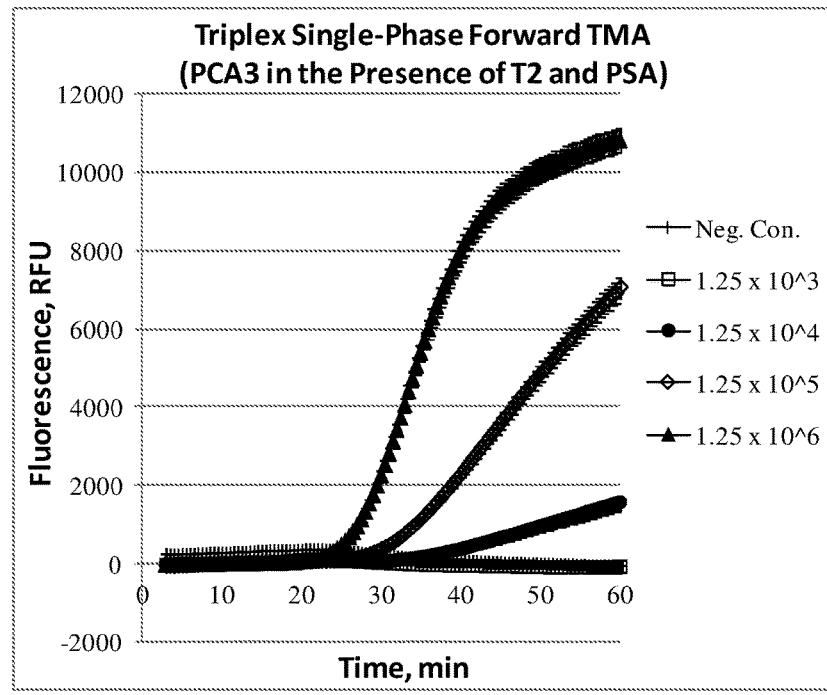
FIGS. 10A-10I show a comparison between the standard single-phase (FIGS. 10A, 10D and 10G) and dual-phase (FIGS. 10B, 10E and 10H) forward TMA used for triplex amplification of PCA3, T2-ERG and prostate specific antigen (PSA).
Figure 10B:
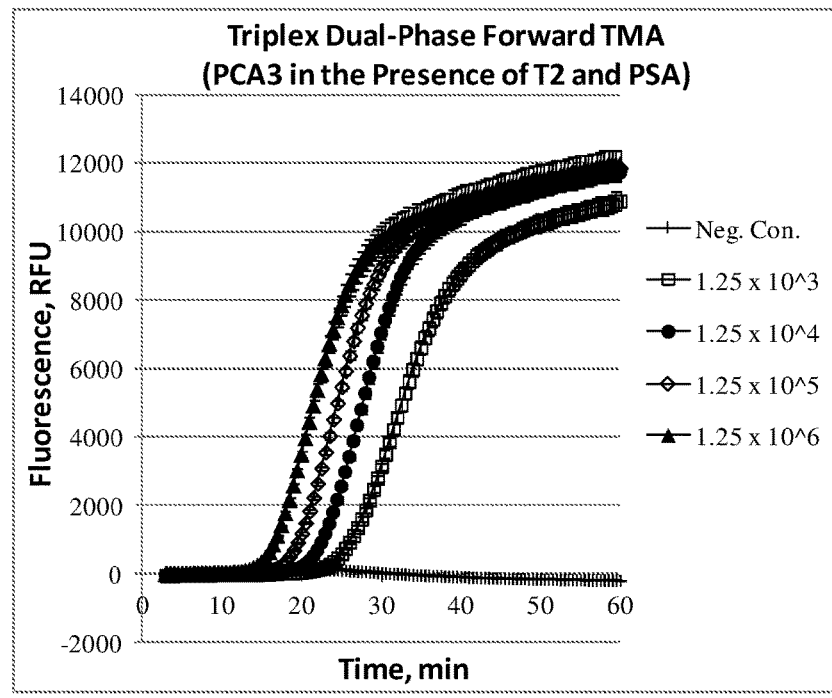
Figure 10C:
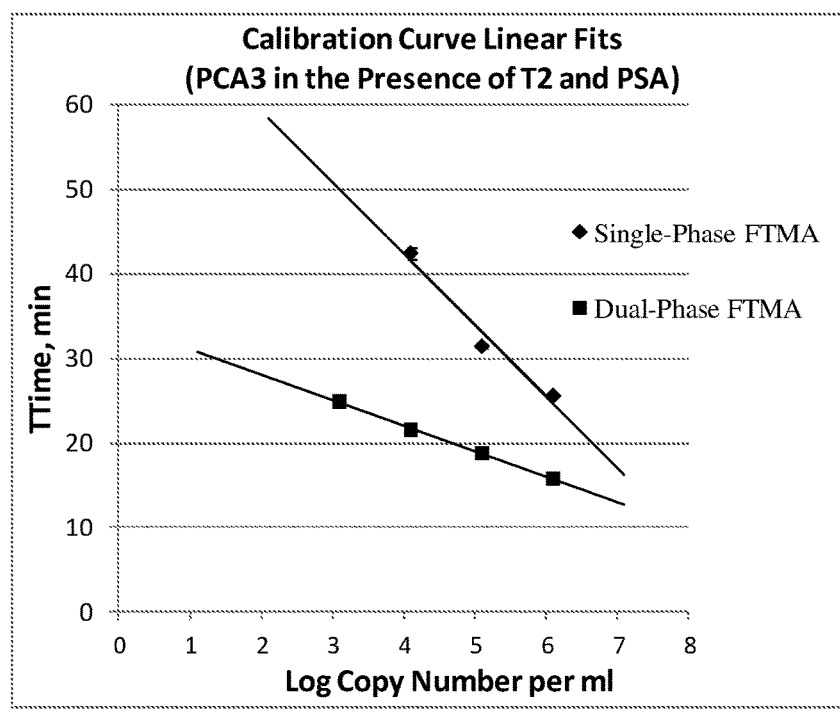

Results of the PCA3 amplification in the presence of PSA and T2-ERG are shown in FIGS. 10A-10C. As shown in FIG. 10A, the single-phase format was able to detect the target template down to ~12,500 copies/mL (~5,000 copies/rxn), whereas the dual-phase format improved the sensitivity 10 fold to ~1,250 copies/mL (~500 copies/rxn) (FIG. 10B). Further, consistent with our prior observations, the dual-phase amplification format was associated with a significant reduction in the time of detection compared with the single-phase format (FIG. 10C).

Figure 10D:
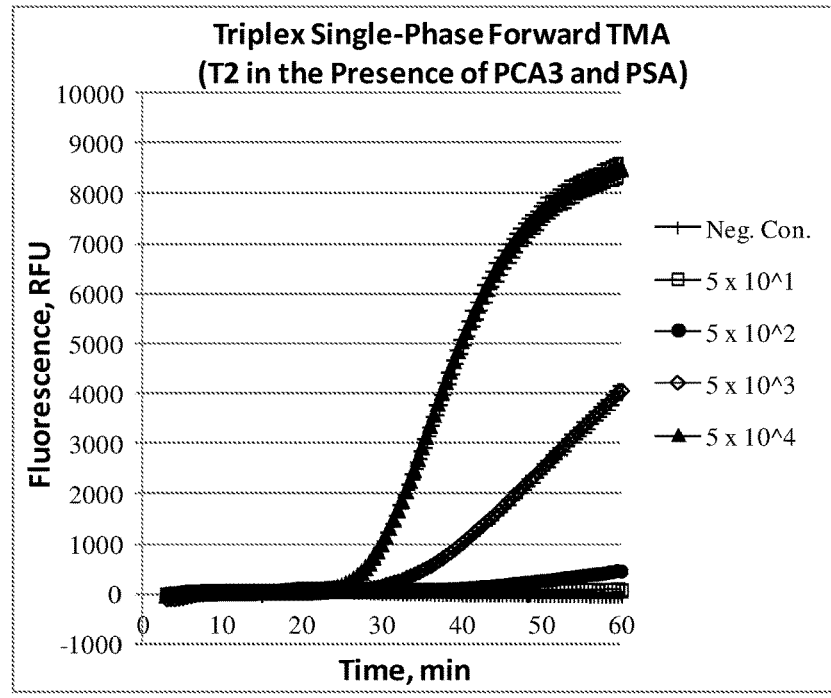
Figure 10E:
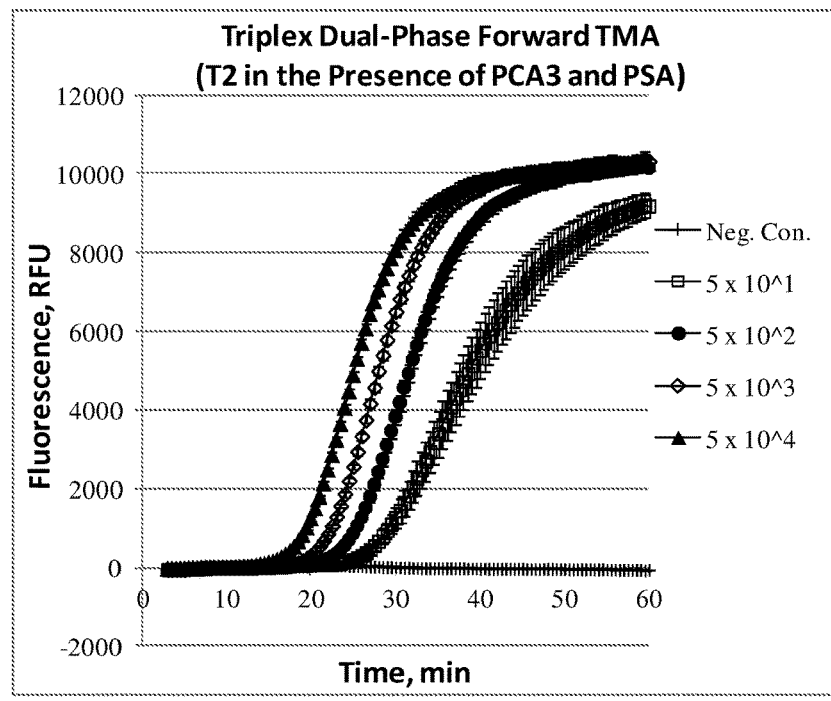
Figure 10F:
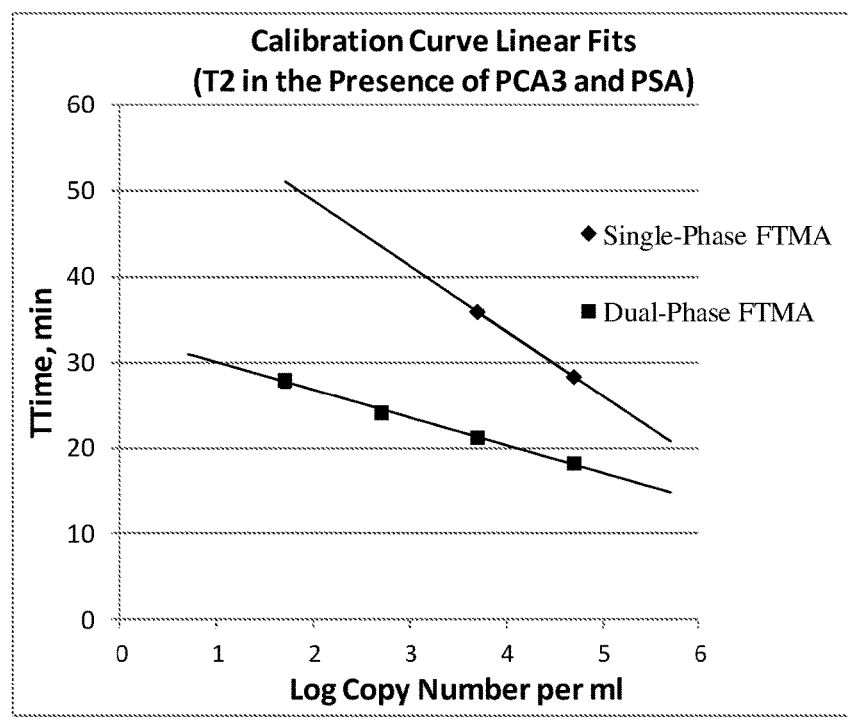

Results of the T2-ERG amplification in the presence of PCA3 and PSA are shown in FIGS. 10D-10F. As shown in FIG. 10D, the single-phase format was able to detect the target template down to ~5,000 copies/mL (~2,000 copies/rxn), whereas the dual-phase format improved the sensitivity 100 fold to ~50 copies/mL (~20 copies/rxn) (FIG. 10E). Further, consistent with our prior observations, the dual-phase amplification format was associated with a significant reduction in the time of detection compared with the single-phase format (FIG. 10F).

Figure 10G:
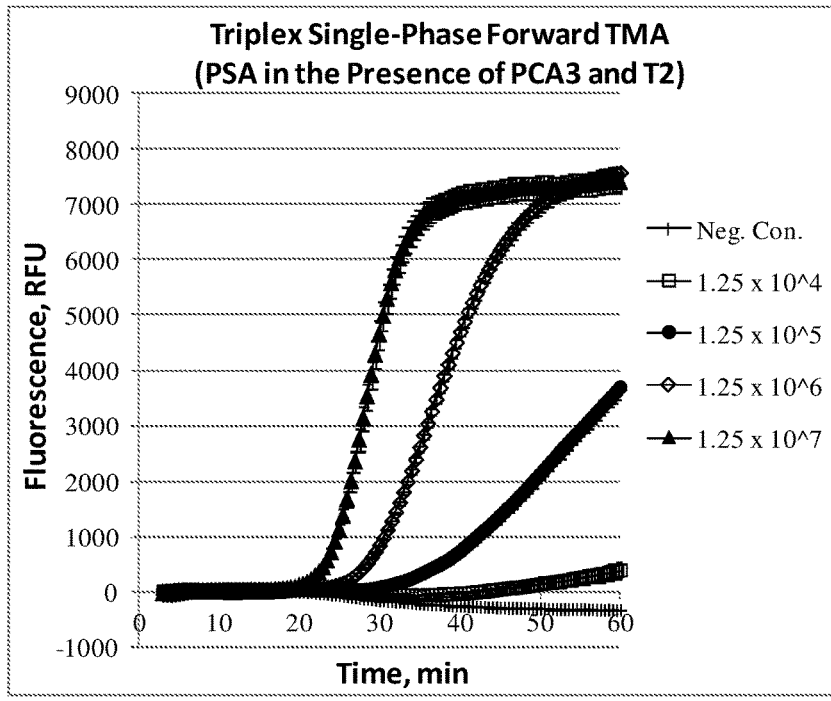
Figure 10H:
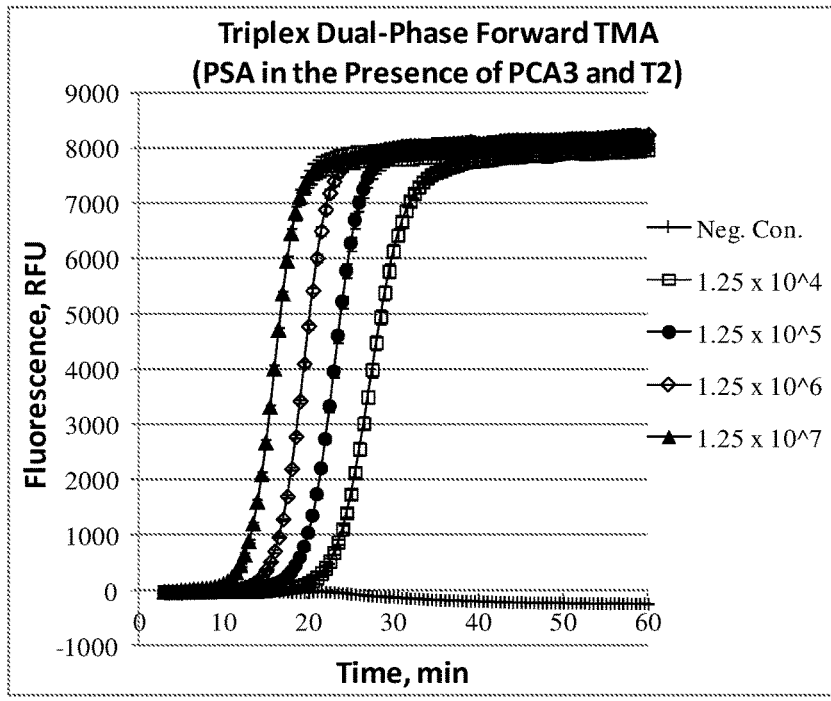
Figure 10I:
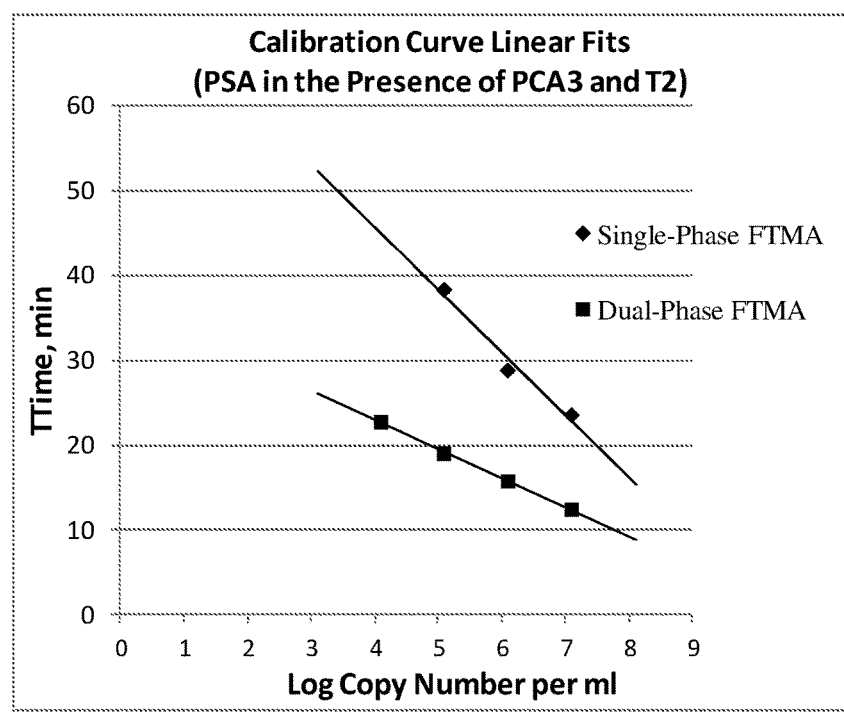

Results of the PSA amplification in the presence of PCA3 and T2-ERG are shown in FIGS. 10G-10I. As shown in FIG. 10G, the single-phase format was able to detect the target template down to ~125,000 copies/mL (~50,000 copies/rxn), whereas the dual-phase format improved the sensitivity over 10 fold to ~12,500 copies/mL (~500 copies/rxn) (FIG. 10H). Further, consistent with our prior observations, the dual-phase amplification format was associated with a significant reduction in the time of detection compared with the single-phase format (FIG. 10I).

Example 8

Amplification of T2-ERG in Dual-Phase Reverse TMA Format

In this example, we tested a dual-phase reverse TMA protocol using T2-ERG as a target template. This is in contrast to all of the preceding working examples, where various forward TMA protocols were employed. The general description of reverse TMA is set forth above in connection with single primer amplification.

In the dual-phase reverse TMA protocol used here, a non-T7 primer was hybridized to the 3' end of the target T2-ERG sequence during target capture, followed by removal of excess non-T7 primer. The amplification process was divided into two distinct phases. During the first phase, a T7 promoter provider was introduced along with all of the requisite amplification, detection and enzyme reagents, with the exception of additional non-T7 primer. The T7 promoter provider was blocked at the 3' end, thereby rendering it impossible to extend it enzymatically. In the presence of reverse transcriptase, the non-T7 primer hybridized to the target was extended, creating a cDNA copy, and the target RNA template was degraded by the reverse transcriptase's RNase H activity. The T7 promoter provider subsequently hybridized to the 3' end of the cDNA, and the 3' end of the cDNA was extended further, filling in the promoter region of the T7 promoter provider and creating an active, double-stranded template. T7 polymerase then produced multiple RNA transcripts from the template that were identical to the target template. Because no non-T7 primer was available in the phase 1 amplification mixture, the reaction could not proceed any further. The second phase was then started with the addition of non-T7 primer, thus initiating exponential amplification of the RNA transcript pool produced in phase 1.

Figure 11A:
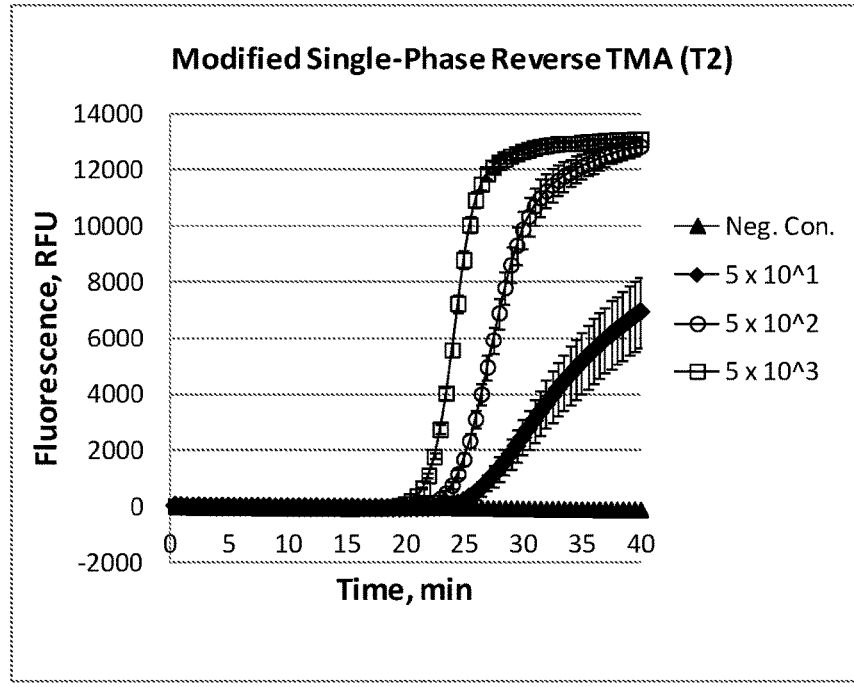
FIGS. 11A-11C demonstrate a comparison between a modified single-phase reverse TMA and dual-phase reverse TMA.
Figure 11B:
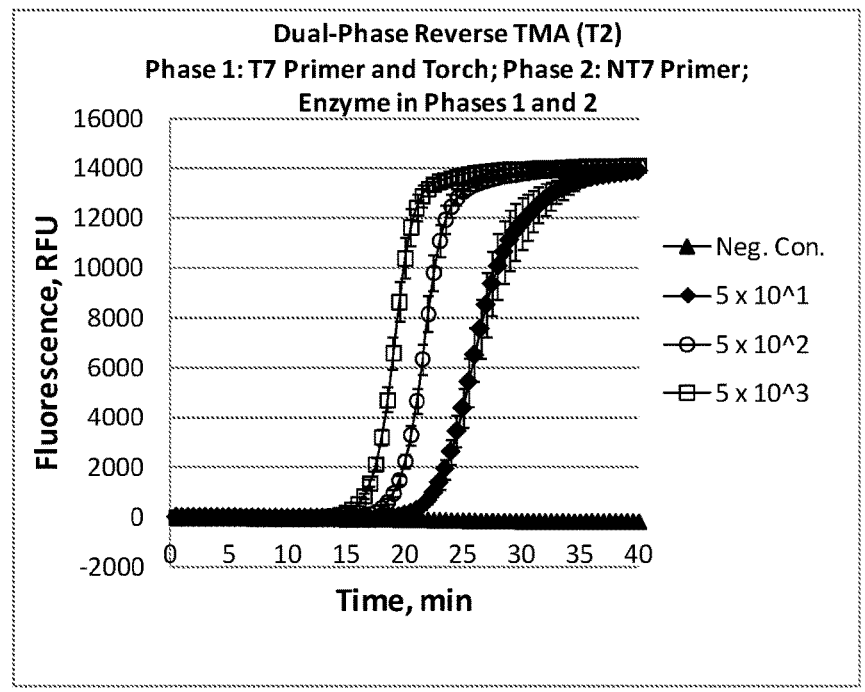
Figure 11C:
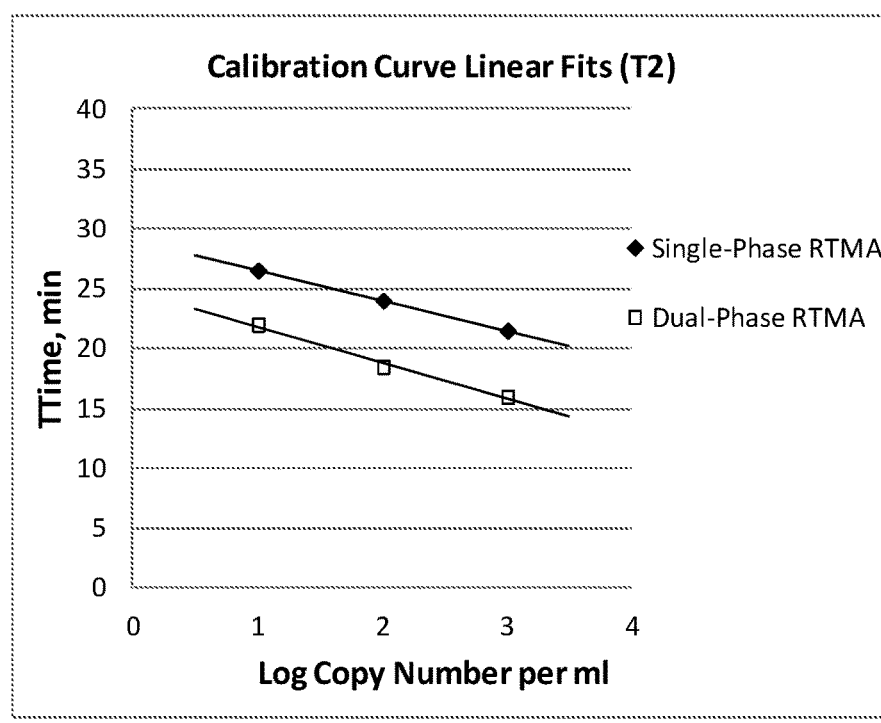

Results from the dual-phase reverse TMA experiment are shown in FIG. 11B. FIG. 11A shows results of a control single-phase reverse TMA experiment that was modified to mimic the dual-phase format. More specifically, the non-T7 primer was added during the target capture step (allowing the standard 60° C. annealing step to be eliminated from the protocol); no primers or Enzyme Reagent were added in the first phase; and non-T7 primer and T7 promoter provider as well as Enzyme Reagent were added to the second phase for the initiation of exponential amplification. As one can see from FIGS. 11A and 11B, the dual-phase reverse TMA format yielded a significantly improved sensitivity and precision at the low end of analyte concentration (~50 copies/rxn) compared with the modified single-phase reverse TMA format. Once again, the dual-phase format yielded superior performance both in terms of precision and shorter detection time (FIG. 11C).

Example 9

Co-Amplification of T2-ERG, PCA3, PSA and CAP in Dual-Phase Reverse TMA Format

In this example, T2-ERG, PCA3, PSA and internal control (CAP) target templates were co-amplified using two different dual-phase reverse TMA protocols to determine whether quadruplex amplification will result in the same improvement in sensitivity and precision we have observed previously in uniplex, duplex an triplex assays (Examples 2-8).

Figure 12A:
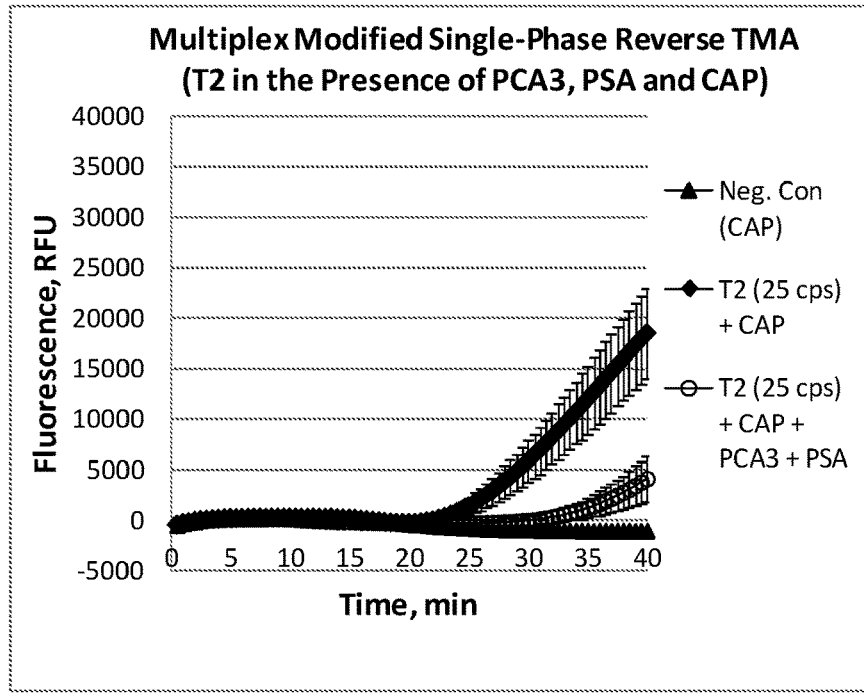
FIGS. 12A-12C show a comparison between the modified single-phase (FIG. 12A), the dual-phase format described in 11 (FIG. 12B), and a different dual-phase format (FIG. 12C) reverse TMA used for quadruplex amplification of T2-ERG, PCA3, PSA and an internal control (CAP).
Figure 12B:
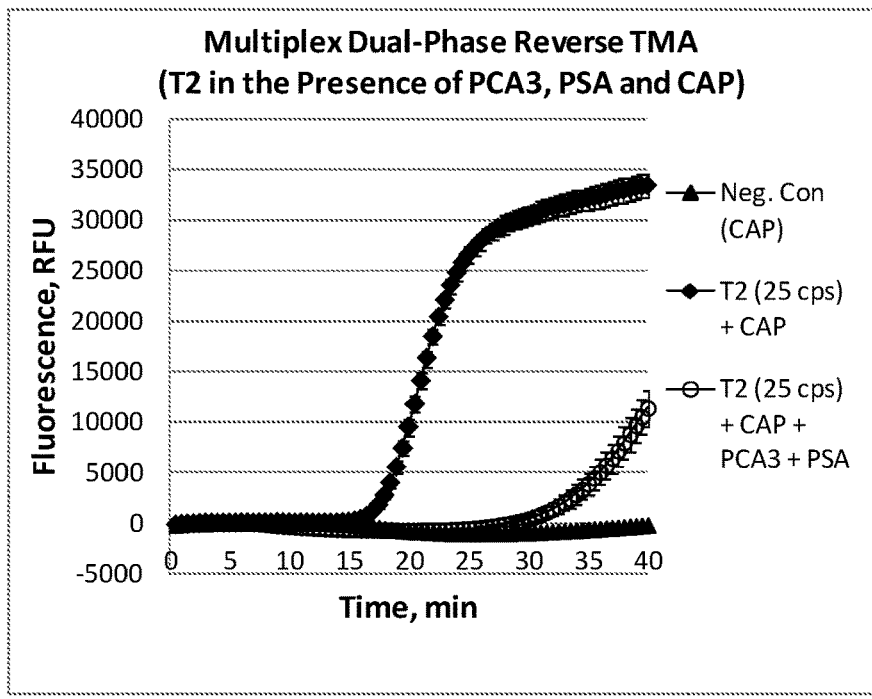
Figure 12C:
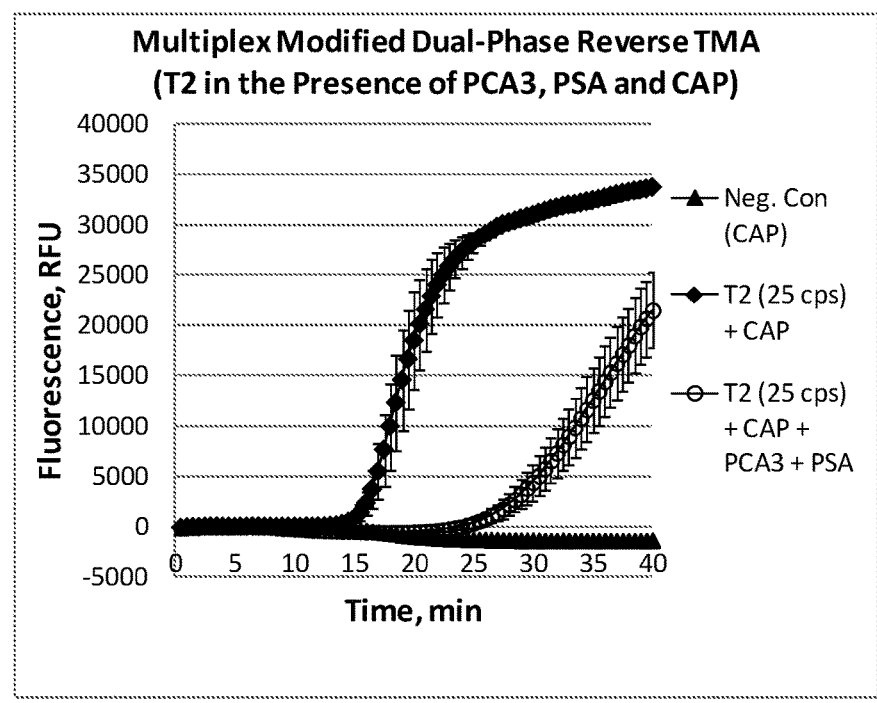

Detection of 25 copies/rxn of T2-ERG, which is notoriously difficult to amplify at low levels in the presence of other targets, is shown in FIGS. 12A-12C in the presence of 500,000 copies/rxn of PCA3, 5,000,000 copies/rxn of PSA and 5,000 copies/rxn of CAP (open circles) or in the presence of 5,000 copies/rxn of CAP alone (solid diamonds). FIG. 12A shows results of a control experiment that was carried out in the modified single-phase reverse TMA format as described above in Example 8. FIG. 12B shows results of a dual-phase experiment using the dual-phase reverse TMA format as also described in Example 8. Briefly, non-T7 primers were hybridized to the target T2-ERG, PCA3, PSA and CAP sequences during target capture, followed by removal of excess non-T7 primers. In the first phase of amplification, T7 promoter providers were added along with all of the requisite amplification, detection and enzyme reagents, with the exception of additional non-T7 primers. After five minutes at 42° C., the non-T7 primers were added to the reaction mixture to initiate the exponential amplification phase, which was also carried out at 42° C. with real-time detection in four different fluorescent channels (one for each target). As one can see from FIGS. 12A and 12B, the dual-phase reverse TMA format yielded an improved sensitivity and precision at 25 copies/rxn T2-ERG in the presence of PCA3, PSA and CAP and a significantly improved sensitivity and precision at 25 copies/rxn T2-ERG in the presence of CAP alone compared with the modified single-phase reverse TMA format. These results also demonstrate that the dual-phase format is effective in reducing analyte-analyte interference in a multiplex reaction. Further, consistent with our prior observations, the dual-phase amplification format was associated with a reduction in the time of detection compared with the single-phase format.

FIG. 12C shows results of a different dual-phase format, where in the first phase of the reaction PCA3, PSA and CAP (or CAP alone) were subjected to linear amplification and T2-ERG was subjected to exponential amplification, and in the second phase PCA3, PSA and CAP were subjected to exponential amplification and T2-ERG continued amplifying exponentially (all four amplification reaction were carried out in the same vessel). The distribution of target-specific primers between the different phases of amplification is set forth in Table 1 below. As one can see from FIGS. 12A and 12C, this different dual-phase reverse TMA format yielded a significantly improved sensitivity at 25 copies/rxn T2-ERG in the presence of PCA3, PSA and CAP, or CAP alone, compared with the modified single-phase reverse TMA format. As with the dual-phase format described in previous examples, these results demonstrate that this different dual-phase format is effective in reducing analyte-analyte interference in a multiplex reaction. Further, this different dual-phase amplification format was associated with a reduction in the time of detection compared with the single-phase format.

TABLE 1

| Analyte | Target Capture | First Phase | Second Phase |
|---|---|---|---|
| T2-ERG | Non-T7 primer | Non-T7 primer + T7 promoter provider | — |
| PCA3 | Non-T7 primer | T7 promoter provider | Non-T7 primer |
| PSA | Non-T7 primer | T7 promoter provider | Non-T7 primer |
| CAP | Non-T7 primer | T7 promoter provider | Non-T7 primer |

Example 10

Co-Amplification of T2-ERG, PCA3, PSA and CAP in Triple-Phase Reverse TMA Format In this example, T2-ERG, PCA3, PSA and internal control (CAP) target templates were co-amplified using dual-phase and triple-phase reverse TMA protocols to determine whether triple-phase amplification might yield additional improvements in sensitivity and/or precision at the low end of analyte concentration.

Figure 13A:
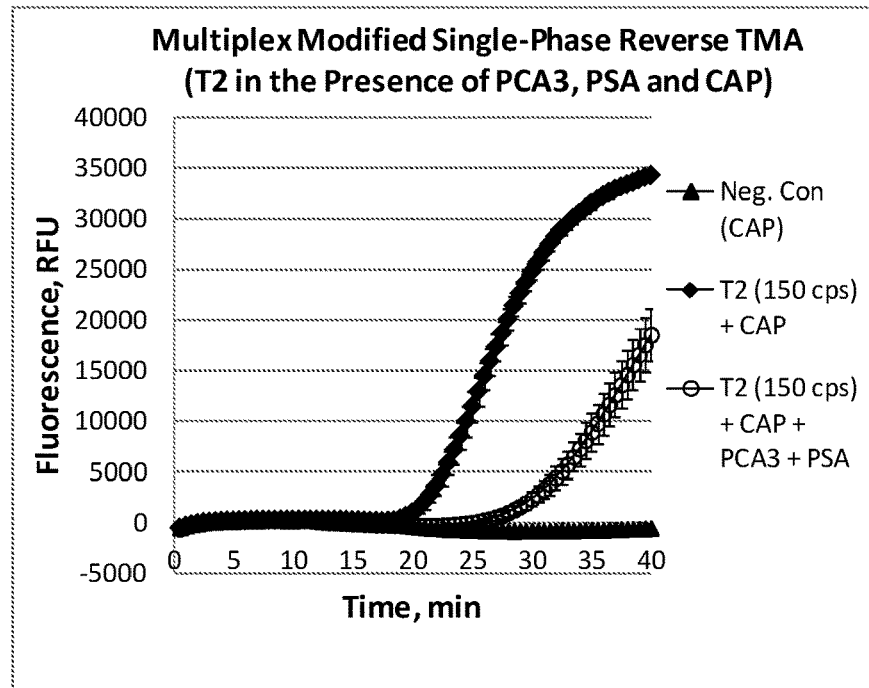
FIGS. 13A-13C show a comparison between the modified single-phase (FIG. 13A), dual-phase (FIG. 13B), and triple-phase (FIG. 13C) reverse TMA used for quadruplex amplification of T2-ERG, PCA3, PSA, and an internal control (CAP).
Figure 13B:
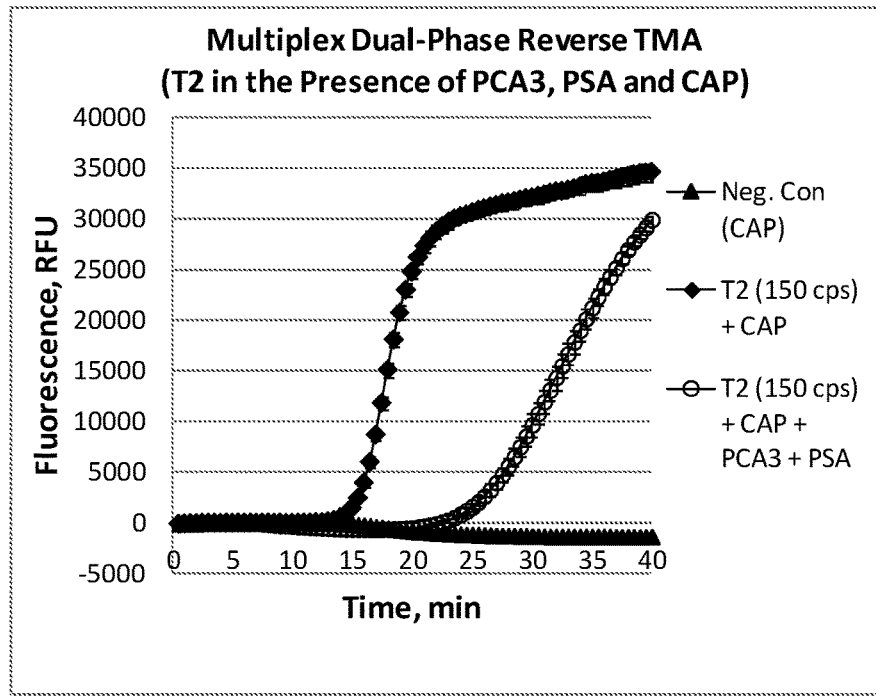
Figure 13C:
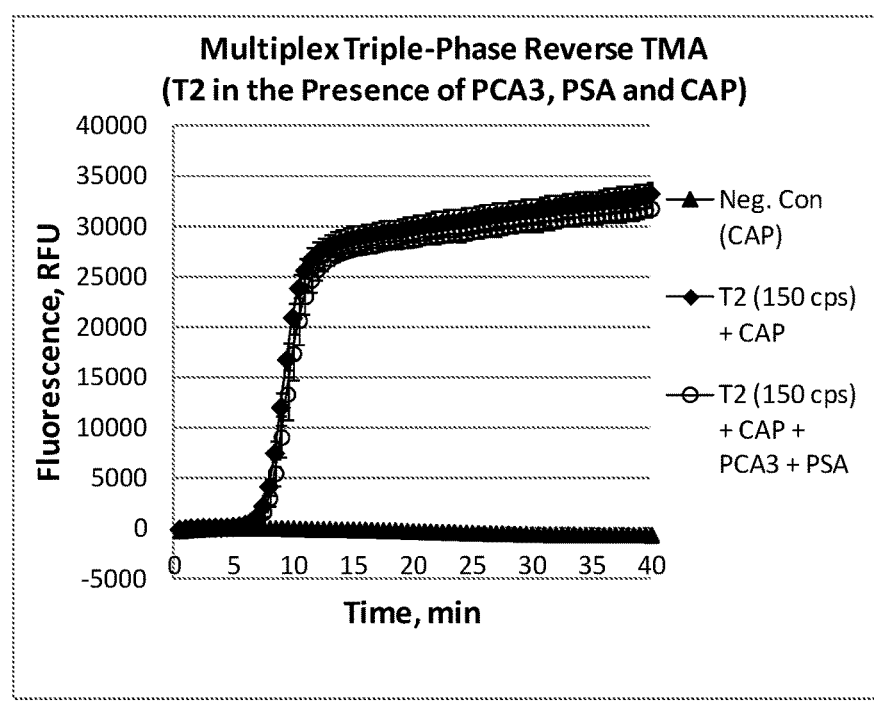

Detection of 150 copies/rxn of T2-ERG is shown in FIGS. 13A-13C in the presence of 500,000 copies/rxn of PCA3, 5,000,000 copies/rxn of PSA and 5,000 copies/rxn of CAP (open circles) or in the presence of 5,000 copies/rxn of CAP alone (solid diamonds). FIG. 13A shows results of a control experiment that was carried out in the modified single-phase reverse TMA format as described above in Example 8. FIG. 13B shows results of a dual-phase experiment using the dual-phase reverse TMA format as also described in Example 8. Sensitivity and precision were improved using the dual-phase format.

FIG. 13C shows results of a triple-phase experiment, where in phase 1 T2-ERG was subjected to linear amplification and the other 3 analytes were not amplified, in phase 2 T2-ERG was subjected to exponential amplification and the 3 other analytes were not amplified, and in phase 3 PCA3, PSA and CAP (or CAP alone) were subjected to exponential amplification and T2-ERG continued amplifying exponentially (all of the amplification reactions proceeded in the same vessel). The distribution of target-specific primers between the different phases of amplification is set forth in Table 2 below. As one can see from FIGS. 13A and 13C, the triple-phase reverse TMA format yielded vast improvements in both sensitivity and precision at 150 copies/rxn T2-ERG in the presence of PCA3, PSA and CAP, or CAP alone, compared with the modified single-phase reverse TMA format. These results also demonstrate that this triple-phase format is effective in reducing analyte-analyte interference in a multiplex reaction. Further, this triple-phase amplification format was associated with a reduction in the time of detection compared with the single-phase format.

TABLE 2

| Analyte | Target Capture | First Phase | Second Phase | Third Phase |
|---|---|---|---|---|
| T2-ERG | Non-T7 primer | T7 promoter provider | Non-T7 primer | — |
| PCA3 | Non-T7 primer | — | — | Non-T7 primer + T7 promoter provider |
| PSA | Non-T7 primer | — | — | Non-T7 primer + T7 promoter provider |
| CAP | Non-T7 primer | — | — | Non-T7 primer + T7 promoter provider |

As illustrated above, a multiphase amplification format has been developed and demonstrated to work for several different nucleic acid targets, as well as combinations of targets. Compared to the standard single-phase format, the multiphase amplification format resulted in significant improvements of limits of detection, which will translate into comparable improvements in the limits of quantitation.

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the appended claims.

What is claimed is:

1. A method of quantifying a target nucleic acid sequence in a sample, comprising the steps of:
    (a) contacting the sample with a first amplification oligonucleotide, specific for a first portion of the target nucleic acid sequence, under conditions allowing hybridization of the first amplification oligonucleotide to the first portion of the target nucleic acid sequence, thereby generating a pre-amplification hybrid that comprises the first amplification oligonucleotide and the target nucleic acid sequence;
    (b) isolating the pre-amplification hybrid by target capture onto a solid support followed by washing to remove any of the first amplification oligonucleotide that did not hybridize to the first portion of the target nucleic acid sequence in step (a);
    (c) amplifying, in a first phase amplification reaction mixture, at least a portion of the target nucleic acid sequence of the pre-amplification hybrid isolated in step (b) in a first phase, substantially isothermal, transcription-associated amplification reaction under conditions that support linear amplification thereof, but do not support exponential amplification thereof, thereby resulting in a reaction mixture comprising a first amplification product,
        wherein the first phase amplification reaction mixture comprises a second amplification oligonucleotide, the second amplification oligonucleotide being complementary to a portion of an extension product of the first amplification oligonucleotide and wherein the second amplification oligonucleotide is not enzymatically extended in the first phase of isothermal transcription-associated amplification reaction, and wherein the first amplification product is not a template for nucleic acid synthesis during the first phase, substantially isothermal, transcription-associated amplification reaction;

(d) combining the reaction mixture comprising the first amplification product with at least one component that participates in exponential amplification of the first amplification product, but that is lacking from the reaction mixture comprising the first amplification product, to produce a second phase amplification reaction mixture, wherein the second phase amplification reaction mixture additionally comprises a sequence-specific hybridization probe;

(e) performing, in a second phase, substantially isothermal, transcription-associated amplification reaction in the second phase amplification reaction mixture, an exponential amplification of the first amplification product, thereby synthesizing a second amplification product;

(f) detecting, with the sequence-specific hybridization probe at regular time intervals, synthesis of the second amplification product in the second phase amplification reaction mixture; and (g) quantifying the target nucleic acid sequence in the sample using results from step (f).

2. The method of claim 1, wherein the first amplification oligonucleotide comprises a 3' target specific sequence and a 5' promoter sequence for an RNA polymerase.

3. The method of claim 1, wherein the RNA polymerase is T7 RNA polymerase.

4. The method of claim 1, wherein the solid support comprises an immobilized capture probe.

5. The method of claim 1,
wherein step (a) further comprises contacting the sample with a target capture oligonucleotide that hybridizes to the target nucleic acid sequence, and
wherein the pre-amplification hybrid comprises the target nucleic acid sequence hybridized to each of the target capture oligonucleotide and the first amplification oligonucleotide.

6. The method of claim 1, wherein the solid support comprises magnetically attractable particles.

7. The method of claim 1, wherein each of the first and second phase isothermal transcription-associated amplification reactions comprise an RNA polymerase and a reverse transcriptase.

8. The method of claim 1, wherein the at least one component comprises the first amplification oligonucleotide.

9. The method of claim 1, wherein the first amplification product of step (c) is a cDNA molecule with the same polarity as the target nucleic acid sequence in the sample, and wherein the second amplification product of step (e) is an RNA molecule.

10. The method of claim 1, wherein the sequence-specific hybridization probe in step (d) is a conformation-sensitive probe that produces a detectable signal when hybridized to the second amplification product.

11. The method of claim 1, wherein the sequence-specific hybridization probe in step (d) is a fluorescently labeled sequence-specific hybridization probe.

12. The method of claim 1, wherein step (g) comprises quantifying the target nucleic acid sequence in the sample using a linear calibration curve and results from step (f).

13. The method of claim 1, wherein step (c) comprises amplifying by 10-fold to 10,000-fold, in the first phase amplification reaction mixture.

14. The method of claim 1, wherein the second amplification oligonucleotide comprises a blocked 3' terminus.

* * * * *